United States Patent [19]

Leumann

[11] Patent Number: 5,393,878
[45] Date of Patent: Feb. 28, 1995

[54] BICYCLIC NUCLEOSIDES, OLIGONUCLEOTIDES, PROCESS FOR THEIR PREPARATION AND INTERMEDIATES

[75] Inventor: Christian Leumann, Zurich, Switzerland

[73] Assignee: Ciba-Geigy Corporation, Ardsley, N.Y.

[21] Appl. No.: 214,737

[22] Filed: Mar. 17, 1994

Related U.S. Application Data

[62] Division of Ser. No. 959,851, Oct. 13, 1992, Pat. No. 5,319,080.

[30] Foreign Application Priority Data

Oct. 17, 1991 [CH] Switzerland ............... 3043/91

[51] Int. Cl.$^6$ ............... C07H 19/06; C07D 239/02; C07D 239/06; C07D 239/22
[52] U.S. Cl. ............... 536/28.2; 536/28.3; 536/28.4; 536/28.5; 536/28.51; 536/28.52; 536/28.53; 536/28.54; 536/28.55; 544/298; 544/309; 544/314; 544/317
[58] Field of Search ............... 536/28.2, 28.3, 28.4, 536/28.5, 28.51, 28.52, 28.53, 28.54, 28.55; 544/298, 309, 314, 317; 514/274, 269

[56] References Cited

U.S. PATENT DOCUMENTS

| | | | |
|---|---|---|---|
| 3,709,874 | 1/1973 | Moffatt et al. | 536/27.1 |
| 4,466,765 | 7/1984 | Naito et al. | 536/26 |
| 4,479,951 | 10/1984 | Klessing et al. | 514/234.2 |
| 4,918,075 | 4/1990 | Zahler et al. | 514/262 |
| 4,971,972 | 11/1990 | Doll et al. | 514/265 |
| 4,975,434 | 12/1990 | Marquez et al. | 514/274 |
| 5,059,690 | 10/1991 | Zahler et al. | 544/276 |

FOREIGN PATENT DOCUMENTS

| | | |
|---|---|---|
| 266099 | 5/1988 | European Pat. Off. |
| 8707300 | 12/1987 | WIPO |
| 8809796 | 12/1988 | WIPO |
| 8908146 | 9/1989 | WIPO |
| 9012014 | 10/1990 | WIPO |
| 9104983 | 4/1991 | WIPO |
| 9106556 | 5/1991 | WIPO |

OTHER PUBLICATIONS

E. Uhlmann et al. Chem. Reviews vol. 90, No. 4 (1990) 543–584.
V. Marquez et al. Medicinal Research vol. 6 No. 1 (1986) 1–40.
Fissekis et al. "Synthesis of 5-Hydroxyalkyl-pyrimedines from Lactones III, 5-Dihydroxycyclee-pentyl Pyrimidines" (1967) pp. 395–3603.

*Primary Examiner*—Douglas W. Robinson
*Assistant Examiner*—Francisco Prats
*Attorney, Agent, or Firm*—George R. Dohmann

[57] ABSTRACT

Compounds of the formula I in the form of the racemates or enantiomers thereof,

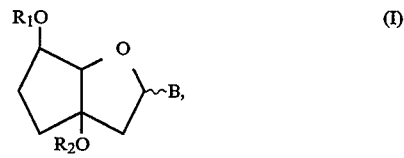

in which $R_1$ and $R_2$ independently of one another are hydrogen or a protective group, and B is a purine or pyrimidine radical or an analogue thereof, can be used as antiviral active ingredients or for the preparation of biologically active oligonucleotides.

14 Claims, No Drawings

BICYCLIC NUCLEOSIDES, OLIGONUCLEOTIDES, PROCESS FOR THEIR PREPARATION AND INTERMEDIATES

This is a divisional of Ser. No. 07/959,851, filed Oct. 13, 1992, now U.S. Pat. No. 5,319,080.

The invention relates to nucleosides having a bicyclo[3,3,0]-8-oxaoctane skeleton, to a process for their preparation by substituting an anomeric leaving group by a nuclein base from the thymine, adenine, purine or cytosine series, to bicyclo[3,3,0]-1,3,5-trihydroxy -8-oxaoctane and the protected derivatives thereof as intermediates, to oligonucleotides having these nucleosides, and to the use of the nucleosides for the preparation of olignucleotides having identical or different nucleoside units in the molecule.

As antiviral active ingredients and due to their capacity of interacting with nucleic acids and the biological activity which this entails, nucleosides and oligonucleotides have been met with widespread interest, see, for example, E. Uhlmann et al., Chemical Reviews, Vol. 90, pages 543 to 584 (1990). To provide nucleosides which have novel properties, or to improve the interaction and stability to nucleases, the sugar radicals of the nucleosides, for example furanoses, have been derivatised in a variety of ways, see, for example, V. E. Marquez et al., Medicinal Research Reviews, Vol. 6, pages 1–40 (1986). Bicyclic furanose derivatives have not been disclosed as yet for this purpose.

The invention relates to compounds of the formula I in the form of the racemates or enantiomers thereof,

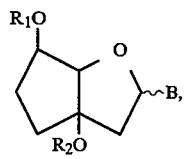

(I)

in which $R_1$ and $R_2$ independently of one another are hydrogen or a protective group, and B is a purine or pyrimidine radical or an analogue thereof.

Protective groups and processes for the derivatisation of the hydroxyl groups having such protective groups are generally known in sugar chemistry. Examples of such protective groups are: linear or branched $C_1$–$C_8$alkyl, in particular $C_1$–$C_4$alkyl, for example methyl, ethyl, n- and i-propyl, or n-, i- and t-butyl; $C_7$–$C_{12}$aralkyl, for example benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, tri(methoxyphenyl)methyl, tri(dimethoxyphenyl)methyl; triphenylsilyl, alkyldiphenylsilyl, dialkylphenylsilyl and trialkylsilyl having 1 to 20, preferably 1 to 12 and particularly preferably 1 to 8, C atoms in the alkyl groups, for example trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl; $C_2$–$C_{12}$acyl, particularly $C_2$–$C_8$acyl, for example acetyl, propanoyl, butanoyl, pentanoyl, hexanoyl, benzoyl, methylbenzoyl, methoxybenzoyl, chlorobenzoyl and bromobenzoyl; $R_3$—$SO_2$—, in which $R_3$ is $C_1$–$C_{12}$alkyl, in particular $C_1$–$C_6$alkyl, $C_5$cycloalkyl or $C_6$cycloalkyl, phenyl, benzyl, $C_1$–$C_{12}$alkylphenyl and, in particular, $C_1$–$C_4$alkylphenyl, or $C_1$–$C_{12}$alkylbenzyl and, in particular, $C_1$–$C_4$alkylbenzyl, or halophenyl or halobenzyl, for example methyl-, ethyl-, propyl-, butyl-, phenyl-, benzyl-, p-bromo-, p-methoxy- and p-methylphenylsulfonyl; $C_1$–$C_{12}$alkoxycarbonyl, preferably $C_1$–$C_8$alkoxycarbonyl, for example methoxy-, ethoxy-, n- or i-propoxy- or n-, i- or t-butoxycarbonyl, or phenyloxycarbonyl, benzyloxycarbonyl, methyl- or methoxy- or chlorophenyloxycarbonyl or -benzyloxycarbonyl. $R_1$ and $R_2$ in formula I can be identical or different protective groups, identical protective groups generally being preferred.

In a preferred embodiment, the compounds of the formula I are those in which $R_1$ and $R_2$ independently of one another are linear or branched $C_1$–$C_4$alkyl, $C_7$–$C_{12}$aralkyl, trialkylsilyl having 1 to 12 C atoms in the alkyl groups, $C_2$–$C_8$acyl, $R_3$—$SO_2$—, in which $R_3$ is $C_1$–$C_6$alkyl, phenyl, benzyl, $C_1$–$C_4$alkylphenyl, $C_1$–$C_4$alkylbenzyl, or halophenyl or halobenzyl, or they are $C_1$–$C_8$alkoxycarbonyl, phenoxycarbonyl or benzyloxycarbonyl.

In a particularly preferred embodiment, $R_1$ and $R_2$ are methyl, ethyl, n- and i-propyl or n-, i- and t-butyl; benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, tri(methoxyphenyl)methyl, tri(dimethoxyphenyl)methyl; trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl; acetyl,- propanoyl, butanoyl, pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methylphenylsulfonyl; methoxy-, ethoxy-, n- or i-propoxy- or n-, i- or t-butoxycarbonyl, or phenyloxycarbonyl, benzyloxycarbonyl, methyl- or methoxy-or chlorophenyloxycarbonyl or -benzyloxycarbonyl.

If B is a purine radical or an analogue thereof, then the radicals can be those of the formulae II, IIa, IIb, IIc, IId or IIe

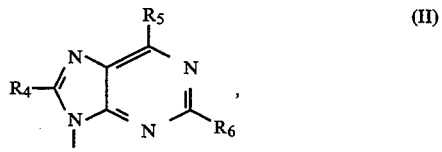

(II)

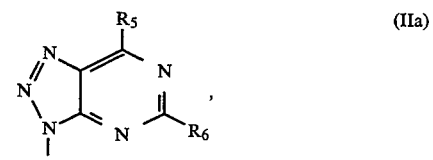

(IIa)

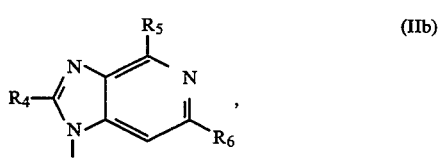

(IIb)

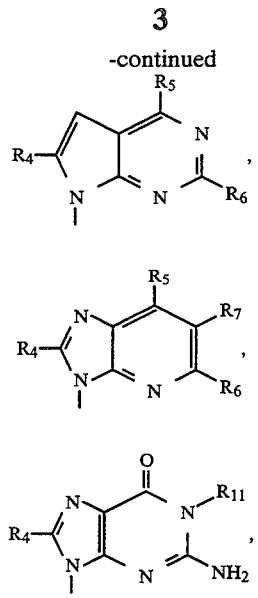

in which $R_4$ is H, Cl, Br or OH, and $R_5$, $R_6$ and $R_7$ independently of one another are H, OH, SH, $NH_2$, $NHNH_2$, NHOH, NHOalkyl having 1 to 12 C atoms, F, Cl, Br, alkyl or hydroxyalkyl or aminoalkyl or alkoxy or alkylthio having 1 to 12 C atoms, the hydroxyl and amino groups being unsubstituted or substituted by a protective group, or are phenyl, benzyl, primary amino having 1 to 20 C atoms or secondary amino having 2 to 30 C atoms, and $R_{11}$ is H or $C_1$-$C_4$alkyl.

Suitable protective groups have been mentioned above. Preferred protective groups are $_1$-$C_8$acyl groups, for example, acetyl, propionyl, butyroyl and benzoyl. $R_{11}$ is preferably H or methyl.

The primary amino has preferably 1 to 12 and particularly preferably 1 to 6 C atoms, and the secondary amino has preferably 2 to 12 and particularly preferably 2 to 6 C atoms.

Some examples of alkyl, alkoxy, alkylthio, hydroxyalkyl and aminoalkyl, each of which has preferably 1 to 6 C atoms, are methyl, ethyl and the isomers of propyl, butyl, pentyl, hexyl, heptyl, octyl, nonyl, decyl, undecyl and dodecyl, as well as corresponding alkoxy, alkylthio, hydroxyalkyl and aminoalkyl radicals. The alkyl, alkoxy, alkylthio, hydroxyalkyl and aminoalkyl has particularly preferably 1 to 4 C atoms. Preferred alkyl, alkoxy, alkylthio, hydroxyalkyl and aminoalkyl radicals are methyl, ethyl, n- and i-propyl, n-, i- and t-butyl, methoxy, ethoxy, methylthio and ethylthio, aminomethyl, aminoethyl, hydroxymethyl and hydroxyethyl.

The primary amino and secondary amino can be, for example, radicals of the formula $R_8R_9N$ in which $R_8$ is H or, independently, has the meaning of $R_9$, and $R_9$ is $C_1$-$C_{20}$alkyl, $C_1$-$C_{20}$aminoalkyl, $C_1$4 $C_{20}$hydroxyalkyl, preferably $C_1$-$C_{12}$alkyl, $C_1$-$C_{12}$aminoalkyl, $C_1$-$C_{12}$hydroxyalkyl, and particularly preferably $C_1$-$C_6$alkyl, $C_1$-$C_6$aminoalkyl or $C_1$-$C_6$hydroxyalkyl; carboxyalkyl or carbalkoxyalkyl, the carbalkoxy group having 2 to 8 C atoms and the alkyl group having 1 to 6, preferably 1 to 4, C atoms; $C_2$-$C_{20}$alkenyl, preferably $C_2$-$C_{12}$alkenyl and particularly preferably $C_2$-$C_6$alkenyl; phenyl, mono- or di($C_1$-$C_4$alkyl- or $C_1$-$C_4$alkoxy)phenyl, benzyl, mono- or di($C_1$-$C_4$alkyl- or $C_1$-$C_4$alkoxy)benzyl; or 1,2-, 1,3- or 1,4-imidazolyl-$C_1$-$C_6$alkyl, or $R_8$ and $R_9$ together are tetra- or penta-methylene, 3-oxa-1,5-pentylene, $-CH_2-NR_{10}-CH_2CH_2-$ or $-CH_2CH_2-NR_{10}-CH_2CH_2-$, in which $R_{10}$ is H or $C_1$-$C_4$alkyl. The amino group in aminoalkyl can be substituted by one or two $C_1$-$C_4$alkyl or $C_1$-$C_4$hydroxyalkyl groups. The hydroxyl group in the hydroxyalkyl can be etherified with $C_1$-$C_4$alkyl.

Examples of alkyl have been given above. Examples of aminoalkyl are aminomethyl, aminoethyl, 1-aminoprop-2-yl or -3-yl, 1-aminobut-2-yl or -3-yl or -4-yl, N-methyl- or N,N-dimethyl- or N-ethyl- or N,N-diethyl- or N-2-hydroxyethyl- or N,N-di-2-hydroxyethylaminomethyl or -aminoethyl or -aminopropyl or -aminobutyl. Examples of hydroxyalkyl are hydroxymethyl, 1-hydroxyeth-2-yl, 1-hydroxyprop-2- or -3-yl, 1-hydroxybut-2-yl, -3-yl or -4-yl. Examples of carboxyalkyl are carboxymethyl, carboxyethyl, carboxypropyl and carboxybutyl, and examples of carbalkoxyalkyl are these carboxyalkyl groups which are esterified with methyl or ethyl. Examples of alkenyl are allyl, but-1-en-3-yl or-4-yl, pent-3- or 4-en-1-yl or -2-yl, hex-3- or -4- or -5-en-1yl or -2-yl. Examples of alkyl- and alkoxyphenyl, or -benzyl, are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl or diethoxybenzyl. Examples of imidazolylalkyl in which the alkyl group has preferably 2 to 4 C atoms are 1,2-, 1,3- or 1,4-imidazolylethyl or -n-propyl or -n-butyl. $R_m$ is preferably H, methyl or ethyl.

Preferred examples of primary amino and secondary amino are methyl-, ethyl-, dimethyl-, diethyl-, allyl-, mono- or di-( 1-hydroxyeth-2-yl)-, phenyl- and benzyl-, acetyl- and benzoyl-amino.

In a preferred embodiment, $R_4$ is hydrogen. In another preferred embodiment, $R_7$ is hydrogen. In another preferred embodiment, $R_5$ and $R_6$ independently of one another are H, F, Cl, Br, OH, SH, $NH_2$, NHOH, $NHNH_2$, methylamino, dimethylamino, benzoylamino, methoxy, ethoxy and methylthio.

Some examples of analogues from the purine series are, besides purine, adenine, N-methyladenine, N-benzyladenine, 2-methyladenine, 2-methylthioadenine, 2-aminoadenine, 3-carbaadenine, 7-carbaadenine, 1-carbaadenine, 6-hydroxypurine, 2-amino-6-chloropurine, 2-amino-6-methylthiopurine, 2-amino-6-hydroxypurine, 3-carba-6-chloropurine, guanine, 2-methylguanine. Particularly preferred are adenine, 2-aminoadenine and guanine.

If B in formula I is an analogue pyrimidine radical, then these are preferably uracil, thymine and cytosine radicals of the formulae III, IIIa and IIIb,

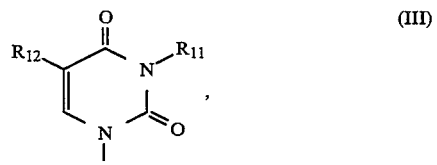

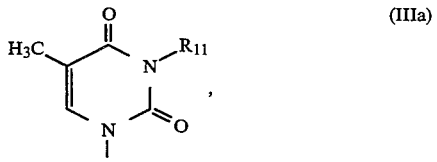

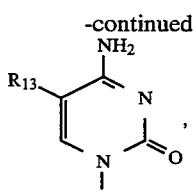

in which $R_{11}$ is H or $C_1-C_4$alkyl, and $R_{12}$ and $R_{13}$ independently of one another are as defined above for $R_5$, including the preferred meanings, and the hydrogen atoms of the $NH_2$ group in formula IIIb can be substituted by $C_1-C_6$alkyl or benzoyl, as well as the dihydro derivatives of the radicals of the formulae III, IIIa and IIIb. $R_{12}$ is preferably H, $C_1-C_6$alkyl or $C_1-C_6$hydroxyalkyl, F, Cl, Br, $NH_2$, benzoylamino, mono- or di-$C_1$-$C_6$alkylamino, and $R_{13}$ is preferably H, $C_1-C_6$alkyl or $C_1-C_6$alkoxy or $C_1-C_6$hydroxyalkyl, F, Cl, Br, $NH_2$, benzoylamino, mono- or di-$C_1$-$C_6$alkylamino.

$R_{11}$ is preferably H or methyl. $R_{12}$ is preferably H, F, Cl, Br, $NH_2$, $NHCH_3$, $N(CH_3)_2$ or $C_1-C_4$alkyl, $R_{13}$ is preferably H, $C_1-C_4$alkyl, in particular methyl, or $NH_2$, $NHCH_3$ or $(CH_3)_2N$.

Some examples of pyrimidine analogues are uracil, thymine, cytosine, 5-fluorouracil, 5-chlorouracil, 5-bromouracil, dihydrouracil, pseudouracil, 1-methylpseudouracil, 5-methyluracil, 3-methylcytosine and 5-methylcytosine.

In a preferred embodiment, the compounds of the formula I are the α- and β-anomers of the formula IV

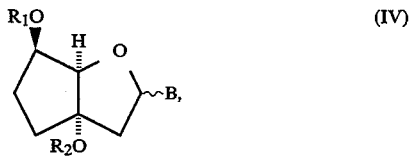

in which $R_1$, $R_2$ and B are as defined above, including the preferred meanings.

In a particularly preferred embodiment, the compounds of the formula IV are the β-anomers of the formula (IVa)

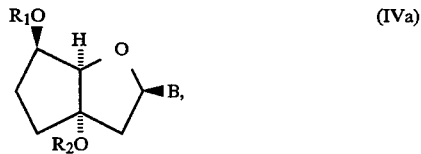

in which $R_1$, $R_2$ and B are as defined above, including the preferred meanings.

The invention furthermore provides a process for the preparation of compounds of the formula I, which comprises reacting a compound of the formula V in the form of the racemates or enantiomers thereof

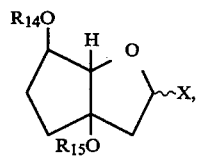

in which $R_{14}$ and $R_{15}$ are identical or different protective groups and X is a leaving group, with a purine, purine analogue or pyrimidine analogue, and, if desired, subsequently removing the protective groups.

Protective groups have been mentioned before. Leaving groups are generally known in sugar chemistry. They can be, for example, halogen, in particular F, Cl, Br or I, $C_1-C_6$alkoxy and, preferably, $C_1-C_4$alkoxy, in particular methoxy or ethoxy, $C_1-C_8$acyloxy, for example acetyloxy, propionyloxy, butyroyloxy; mono- or di- or trichloroacetyloxy or -fluoroacetyloxy, benzoyloxy and chlorobenzoyloxy, or $R_{16}$—$SO_3$, in which $R_{16}$ is $C_1-C_6$alkyl or $C_1-C_6$haloalkyl, or phenyl or benzyl, each of which is unsubstituted or substituted by one to three halogen (F, Cl and Br), $C_1-C_4$alkyl or $C_1-C_4$alkoxy. Examples of haloalkyl are mono- or di- or trichloromethyl or -fluoromethyl, 1,1,1-trichloro- or -trifluoromethyl and pentafluoroethyl. Examples of substituted phenyl and benzyl are methyl-, dimethyl-, methoxy-, dimethoxy-, mono- and dichloro- and mono- and dibromo- and mono- and difluorophenyl and -benzyl. The protective groups and the leaving groups can be identical, in particular in the case of acyl radicals.

The reaction can be carried out at temperatures from −20° to 150° C., preferably 0° to 100° C.

In general, a solvent is used which is preferably aprotic, even more preferred, a solvent which is also dipolar. Examples of solvents which can be used on their own or in the form of a mixture of at least two solvents are ethers (dibutyl ether, tetrahydrofuran, dioxane, diethylene glycol dimethyl ether, ethylene glycol dimethyl ether or ethylene glycol diethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethyl acetate, γ-butyrolactone, δ-valerolactone, pivalolactone), carbonamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (triethylamine, N-methylpiperidine, N-methylmorpholine), aromatic hydrocarbons, such as benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile), as well as aliphatic or cycloaliphatic hydrocarbons (pentane, petroleum ether, hexane, cyclohexane and methylcyclohexane).

Preferred solvents are halogenated aliphatic hydrocarbons, aromatic hydrocarbons, ethers and nitriles, for example methylene chloride, chloroform, benzene, toluene, acetonitrile, diethyl ether, dibutyl ether, tetrahydrofuran and dioxane.

The reaction is preferably carried out in the presence of agents which activate the reactive NH group. Such agents are, for example, inorganic bases (NaOH, KOH, $Na_2CO_3$, $K_2CO_3$, $NaHCO_3$ and $KHCO_3$ as well as alkali metal alcoholates, such as $NaOCH_3$ or $NaOC_4H_9$) or N,O-silylated carboxamides [N,O-bis-(trimethylsilyl)acetamide], disilazanes (hexamethyldisilazane), chlorosilanes (trimethylchlorosilane) and silyl trifluoromethanesulfonates (trimethylsilyl trifluoromethanesulfonate), which can be used on their own or in the form of a mixture or together with Lewis acids, such as BF₃, SbF₃, SbCl₅, TiCl₄ or SnCl₄. It is furthermore possible to metalate the reactive NH group with the aid of, for example, alkali metal hydrides or lithium alkyl compounds (for example LiH, NaH, KH, LiCH₃ LiC₄H₉ ).

In detail, the reaction can be carded out in such a manner that a base B is introduced into a solvent, the activating agents are added, and the mixture is then treated with a compound of the formula V, whereupon the reaction is allowed to proceed to completion. To isolate the compounds of the formula I, the reaction mixture is then worked up in a manner known per se, it being possible to use chromatographic methods for the preparation of pure isomers, particularly of the α- and β-anomers. The enantiomers, for example those of the formula IV, can be obtained by using suitable enantiomers of the formula V. As a rule, the reaction gives a mixture of the αγ- and β-anomers.

The invention furthermore relates to the compounds of the formula V, which are novel, together with the precursors in which R₁₄ and R₁₅ are H and X is OH. The invention therefore furthermore relates to compounds of the formulae V and Va in the form of the racemates or enantiomers thereof,

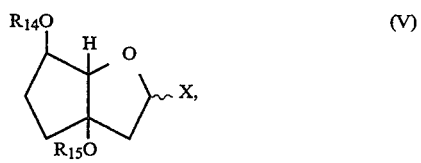
(V)

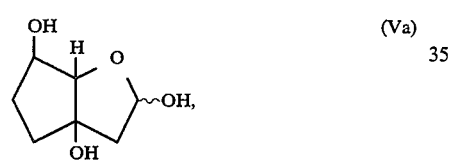
(Va)

in which R₁₄ and R₁₅ are identical or different protective groups and X is a leaving group. Protective groups and leaving groups have been mentioned above. A preferred leaving group is CH₃C(O)O.

In a preferred embodiment, the compounds of the formulae V and Va are the enantiomers of the formulae VI and VIa

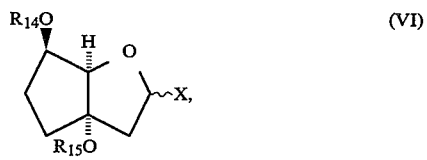
(VI)

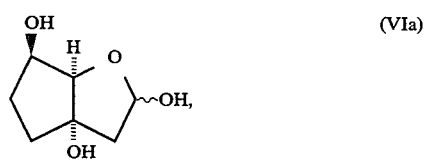
(VIa)

in which R₁₄, R₁₅ and X are as defined above.

The invention furthermore provides the novel process below by which, for example, the compounds of the formulae V, Va, VI and VIa can be prepared.

(±)-Cis-2,3-(2′,2′-isopropyldioxolyl)cyclopentan-1-one, of the formula A,

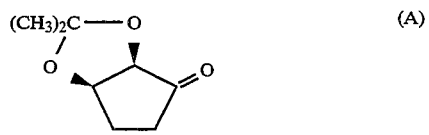
(A)

which has been described in Helv. Chim. Acta 55, page 2838 (1972) by F. G. Cocu et al., is reacted, in a solvent such as tetrahydrofuran, in the presence of approximately 2 equivalents of azabicycloalkenes (for example 1,5,7-triazabicyclo[4,4,0]dec-5-ene) at room temperature, with a β-alkoxycarbonylethylphosphonate (for example diethyl β-ethoxycarbonylethylphosphonate) to give a (±)-cis-2,3-(2′,2′-isopropyldioxolyl)cyclopent-5-ene, for example of the formula B

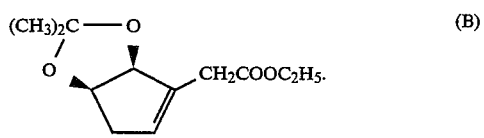
(B)

The cyclopentene derivative is then epoxidised, for example using peracids or H₂O₂, expediently at room temperature or with ice cooling, in a halogenated hydrocarbon as the solvent. In this process, mostly the corresponding (±)-exoepoxide of the cyclopentene derivative is formed, for example of the formula C

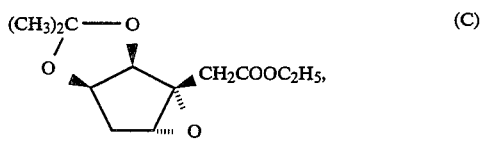
(C)

which only comprises small amounts of the endoepoxide, which can be separated off easily.

The (±)-exoepoxide can be further processed directly by hydrogenation of the carboxylate group to give the primary alcohol group combined with simultaneous hydrogenation of the epoxide group, racemates being obtained. Alternatively, the racemate of the exoepoxide can also be separated into the (+) and (−) enantiomers before the hydrogenation. In this way, not only the nucleoside racemates, but also (−) enantiomers of the natural series and (+) enantiomers of the unnatural series are accessible. The hydrogenation is carried out here in a manner known per se, for example using LiH, NaH, AlH₃, BH₃, LiBH₄, LiAlH₄, di-n-butylaluminium hydride, or else catalytically, using hydrogen.

The racemate can be resolved in a simple manner and in high yields by partial hydrolysis of the carboxylate group using alkali metal hydroxides, for example NaOH, in the presence of porcine liver esterase (EC 3.1.1.1) and NaH₂PO₄ buffer in aqueous phase. This gives a mixture of a carboxylic acid of the formula D

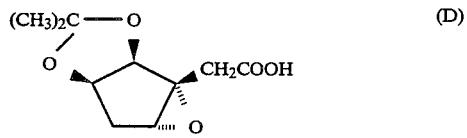
(D)

or of an alkali metal salt thereof with a carboxylate, for example of the formula E

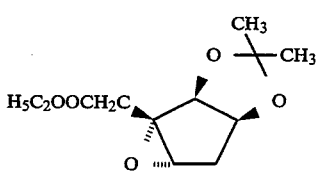

from which the ester can be separated easily by extraction with an organic solvent, for example diethyl ether.

The racemates or the (−) enantiomers (3S,4R,5S configuration) of the formula F and (+) enantiomers (3R,4S,5S configuration) of the formula G

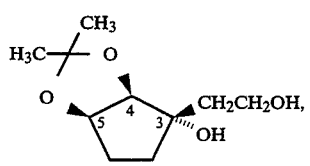

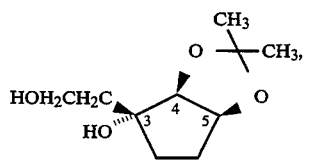

which are obtained in the hydrogenation are oxidised with specific oxidants, for example 1,1,1-triacetyloxy-1,1-dihydro-1,2-benziodoxol-3(1H)-one (Dess-Martin reagent), to give the aldehydes of the formulae H or J of the racemate,

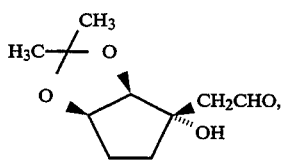

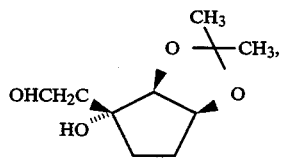

which are hydrolysed and cyclised in the presence of aqueous acids or acidic ion exchangers in the presence of water to give the compounds of the formulae Va or VIa.

Using methods generally known in sugar chemistry, the compounds of the formulae Va and VIa can be converted into compounds of the formulae V or VI by first replacing the anomeric hydroxyl group by a leaving group X and then introducing the protective groups $R_{14}$ and $R_{15}$. If the leaving group and the protective groups are identical, the groups can be introduced in one process step. The compounds of the formulae V and VI can be separated into the α- and β-isomers for example by means of chromatographic methods. Since the reaction with the bases B again give mixtures of the α- and β-forms, it is expedient to carry out this separation only with the compounds of the formula I, or IV. The separability can be improved by deprotecting and by introducing other protective groups.

Before the compounds of the formulae I, IV or IVa are further processed, or for the purpose of their use as pharmaceutical active ingredients, the compounds of the formulae I, IV or IVa are deprotected in the known manner, giving compounds in which $R_1$ and $R_2$ are hydrogen. Using these compounds, oligonucleotides can be constructed which have valuable biological activities due to their interaction with nucleic acids and which can be used as pharmaceutical active ingredients or as diagnostics.

The invention furthermore relates to the use of the compounds of the formula I in the form of racemates or enantiomers for the preparation of oligonucleotides which comprise identical or different monomer units of compounds of the formula I or monomer units of other nucleosides, the oligonucleotides comprising 2 to 200 monomer units. The oligonucleotides preferably contain 2 to 100, particularly preferably 2 to 50, and especially preferably 2 to 20, monomer units. Identical or different monomer units of compounds of the formula I are preferred, identical monomer units of compounds of the formula I being particularly preferred.

The invention furthermore relates to oligonucleotides of the formula VII

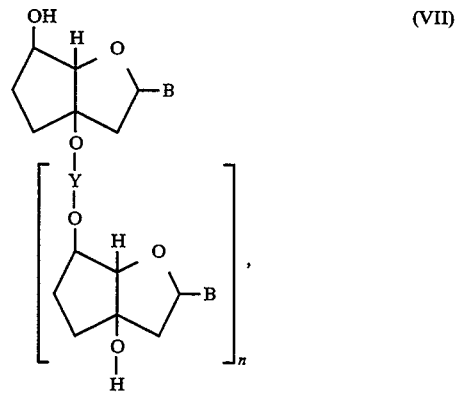

in which B is a purine or pyrimidine radical or an analogue thereof, n is a number from 2 to 200 and Y is a nucleotide bridging group. The preferred meanings and examples given above for compounds of the formula I apply to B. A preferred bridging group is the group -P(O)O⊖-which can be found in natural oligonucleotides. Examples of other bridging groups are -P(O)S⊖-, -P(S)S⊖-, -P(O)$R_{17}$-, -P(O)O$R_{18}$-, -P(O)NR$_{19}$R$_{20}$-, -CO- or -CON(R$_{18}$)$_2$-, in which $R_{17}$ is H or $C_1$-$C_6$alkyl and $R_{18}$ is $C_1$-$C_6$alkyl and $R_{19}$ and $R_{20}$ independently of one another have the meaning of $R_{17}$. In formula VII, n is preferably a number from 2 to 100, particularly preferably a number from 2 to 50 and especially preferably a number from 2 to 20.

In a preferred embodiment, the oligonucleotides of the formula VIIa according to the invention are

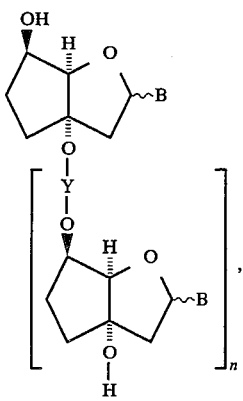

(VIIa)

in which B, Y and n are as defined above, including the preferred meanings. In a particularly preferred embodiment, the oligonucleotides of the formula VIIb according to the invention are

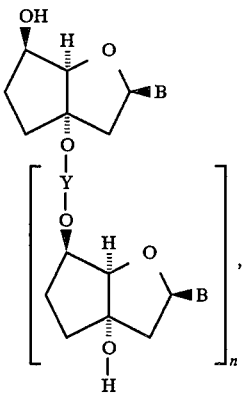

(VIIb)

in which B, Y and n are as defined above, including the preferred meanings. Particularly preferred oligonucleotides of the formula VIIb are those in which B is 9-adenyl and n is 10, or B is cytosyl and n is 6, or B is thymidyl and n is 10.

The oligonucleotides according to the invention can be prepared in the manner known per se by a variety of processes in DNA synthesisers which may be automatised and which are commercially available together with process protocols. In the case of the bridging group -P(O)O$^{\ominus}$-, for example, the phosphorus triester process, the phosphite triester process or the H-phosphonate process can be used, and these are familiar to a person skilled in the art. In the phosphite triester process, for example, a procedure can be followed in which the nucleosides of the formula I in which $R_1$ and $R_2$ are in each case H, are reacted in the form of the racemates or enantiomers thereof, with a protective group reagent, for example 4,4'-dimethoxytriphenylmethyl trifluoromethylsulfonate (abbreviated DMT triflate) to give a nucleoside of the formula K

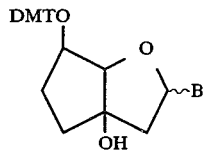

(K)

and the compound of the formula K is bound to a solid carrier, for example to controlled pore glass (CPG) which contains long-chain alkylamino groups, with the aid of a linker, for example succinic anhydride. In a separate process, the hydroxyl group of the compound of the formula K is derivatised, for example to give a phosphoramidite, using [R'O(i-propyl$_2$N)]PCl, to give a compound of the formula L

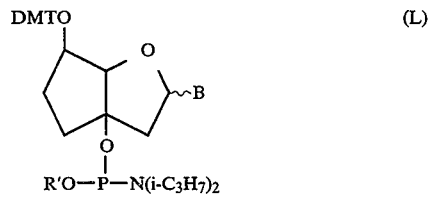

(L)

in which R' is, for example, allyl or β-cyanoethyl.

After the protective group has been split off from the material bound to the carrier, the product is coupled with the compound of the formula L while splitting off —N(i-C$_3$H$_7$), any free hydroxyl groups which may be present are capped, and the phosphite formed is then oxidised to give the phosphate. After the dimer has been deprotected, the reaction cycle with the compound L is repeated until an oligomer has been synthesised which has the desired number of monomer units, and the product is removed from the carrier.

The compounds of the formula I according to the invention in which $R_1$ and $R_2$ are in each case H, have antiviral and antiproliferative properties and can therefore be used as pharmaceuticals. The oligonucleotides according to the invention have an increased stability to degradation by nucleases (for example enzymes). Very good pairing with nucleic acids, in particular double-strand nucleic acids, with the formation of stable triple helices is furthermore observed. The oligonucleotides according to the invention are therefore particularly suitable for antisense technology for the inactivation of nucleoside sequences in nucleic acids (see EP-A-0 266 099, WO 87/07 300 und WO 89/08 146). They can be used for treating infections and diseases, for example by blocking bioactive proteins at the nucleic acid level (for example oncogens). The oligonucleotides according to the invention are also suitable as diagnostics and can be used as gene probes for the detection of vital infections or genetically determined diseases by selective interaction at the level of single- or double-strand nucleic acids. Due to the increased stability to nucleases, a diagnostic application is possible, in particular, not only in vitro, but also in vivo (for example tissue samples, blood plasma and blood serum). Such potential applications are described, for example, in WO 91/06 556.

The invention furthermore relates to the use of the oligonucleotides according to the invention as diagnostics for the detection of viral infections or genetically caused diseases.

The invention furthermore also relates to the nucleosides according to the invention of the formulae I, IV or VIa or of the oligonucleotides of the formulae VII, VIIa or VIIb for use in a therapeutic method for the treatment of diseases in warm-blooded species including humans by inactivation of nucleotide sequences in the body. The dosage rate used when administered to warm-blooded species of a body weight of approximately 70 kg can be, for example, 0.01 to 1000 mg per day. Administration is preferably effected parenterally, for example intravenously or intraperitoneally, in the form of pharmaceutical preparations.

The invention furthermore relates to a pharmaceutical preparation comprising an effective amount of a nucleoside of the formulae I, IV or IVa or of an oligonucleotide of the formulae VII, VIIa or VIIb, as pure active ingredient or together with other active ingredients, a pharmaceutical carder, preferably in a significant amount, and, if desired, adjuncts.

The pharmacologically active nucleosides and oligonucleotides according to the invention can be used in the form of preparations which can be administered parenterally, or of solutions for infusion. Such solutions are preferably isotonic aqueous solutions or suspensions, it being possible for these to be prepared prior to use, for example in the case of lyophilised preparations which comprise the active ingredient as pure active ingredient or together with a carder, for example mannitol. The pharmaceutical preparations can be sterilised and/or comprise adjuncts, for example preservatives, stabilisers, wetting agents and/or emulsifiers, solubilisers, salts for regulating the osmotic pressure and/or buffers. The pharmaceutical preparations which, if desired, can comprise further pharmacologically active ingredients, such as antibiotics, are prepared in the manner known per se, for example by means of conventional dissolving or lyophilisation methods, and comprise approximately 0.1% to 90%, in particular from approximately 0.5% to approximately 30%, for example 1% to 5%, of active ingredient(s).

The examples which follow illustrate the invention. The $^1$H NMR spectra are based on the numbering of the carbon atoms in the following cyclic carbon skeletons:

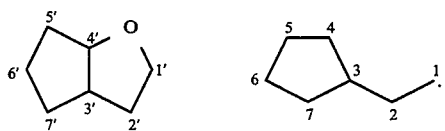

A) PREPARATION OF INTERMEDIATES

Example A 1:

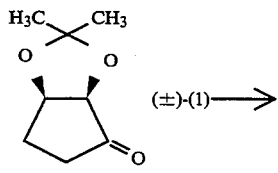

1.4 ml (7 mmol) of triethyl phosphonoacetate and 1.0 g (6.4 mmol) of the compound (1) dissolved in 20 ml of methylene chloride are added at room temperature under a nitrogen atmosphere to a solution of 1.87 g (13.5 mmol) of 1,5,7-triaza-bicyclo[4.4.0]dec-5-ene in 20 ml of methylene chloride. After 3 hours, the reaction mixture is diluted with 70 ml of methylene chloride and washed with 100 ml portions of saturated sodium chloride solution and water. The aqueous phase is extracted with twice 100 ml of methylene chloride. The combined organic phases are dried over MgSO$_4$, filtered and evaporated in vacuo. The oil obtained is chromatographed on silica gel (hexane/ethyl acetate 3:1 ). The solvent is then removed in vacuo, and the oil is dried overnight under a high vacuum. 1.3 g (90%) of the compound (2) are obtained as a colourless oil.

$^1$H NMR (400 MHz, CDCl$_3$): 1.27 [t, J=7,5 H$_3$C—CH$_2$]; 1.36 and 1.38 [2s,2 CH$_3$C]; 2.48 [dd, J=1.0, J=17.8, HC(6)] and 2.59 [dd, J=5.4, J=17.8, HC(6)];3.17[d, J=16.3,H$_2$—C(2)]; 3.22 [d, J=16.3, H$_2$—C(2)]; 4.15 [q, J=7.15, H$_3$C—CH$_2$]; 4.75 [t, J=5.5,HC(5)];5.07 [d, J=5.7, HC(4)]; 5.61 [s broad, HC(7)].

Example A2:

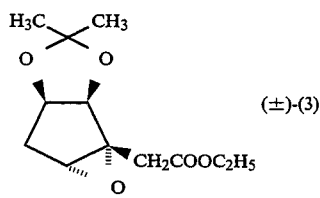

11.5 g (36.55 mmol) of 3-chloroperbenzoic acid dissolved in 100 ml of methylene chloride are added in the course of 10 minutes at 0° C. to a solution of 4.13 g ( 18.27 mmol) of the compound (2) in 200 ml of methylene chloride. After 10 minutes, the ice-bath is removed, and stirring of the reaction mixture is continued for 4 days at room temperature. The reaction is stopped by an addition of 200 ml of 1M aqueous NaHCO$_3$, the organic phase is separated off and the aqueous phase is extracted with twice 150 ml of methylene chloride. The combined organic phases are dried over Na$_2$SO$_4$, filtered and evaporated in vacuo. The oil obtained is chromatographed on silica gel (hexane/ethyl acetate 4:1 ). After removal of the solvent and drying the product in a high vacuum, 3.39 g (76%) of the title compound are obtained as a colourless oil.

$^1$H NMR (400 MHz, CDCl$_3$): 1.28 [t, J=7.14 H$_3$C—CH$_2$]; 1.31 and 1.46 [2s, H$_3$C—CH$_2$ ]; 1.99 [dt, J$_t$=2.1, J$_d$=15.4, HC(6)]; 2.28 [dd, J=6.0, J=15.4, HC(6)]; 2.69 [d, J=16.2,HC(2)]; 3.08 [d, J=16.2, HC(2)]; 3.59 [s broad, HC(7)]; 4.18 [q, J=7.14, H$_3$C—CH$_2$]; 4.56[m, (tripletoid), HC(5)]; 4.65 [d, J=6.0, HC(4)].

Example A3:

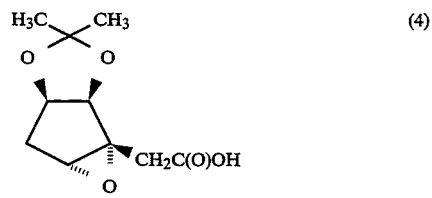

1M NaOH is added to a vigorously stirred emulsion of 10.1 g (41.3 mmol) of the compound (3) in 500 ml of 0.1M phosphate buffer and 1.1 ml (11 mg of protein) porcine liver esterase (EC 3.1.1.1; FLUKA AG Buchs) in such a manner that the pH is constantly 7.75. After 20 ml of 1M NaOH (20 mmol) have been added, the pH is brought to 9.0 using 2N NaOH, and the ester which has not been hydrolysed is extracted with four times 250 ml of diethyl ether. The aqueous phase is then brought to pH 2.0 using 1M HCl, saturated with sodium chloride and extracted six times using 250 ml portions of methylene chloride. The organic phase is dried over Na2SO4, filtered, evaporated in vacuo and dried under a high vacuum. 4.7 g (53%) of the title compound are obtained as a colourless oil.

¹H NMR (200 MHz, C6D6): i.a. 1.10 and 1.36 [2s, H3C—C]; 1.71 dt, J$_t$=1, J$_d$=7.5,HC(6)]; 1.89 [dd, J=3, J=7.5, HC(6)]; 2.45 and 3.00 [2d, J=16.5, HC(2)]; 3.07 [s broad,HC(7)]; 4.24 [dt, J=1, J=3 HC(5)]; 4.63 [d, J=3, HC(4)].

Example A4:

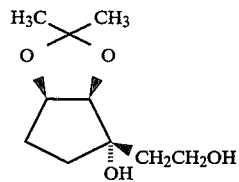

(5)

4.2 g (110.7 mmol) of LiAlH4 are suspended in 60 ml of diethyl ether under a nitrogen atmosphere and in the course of 20 minutes at −30° C. 4.7 g (21.9 mmol) of the compound 4, dissolved in 80 ml of diethyl ether and 20 ml of methylene chloride, are added. When the addition is complete, the cooling bath is removed, and the mixture is stirred for 6 hours at reflux temperature. 20 ml of water and 10 ml of 2M NaOH are then added at room temperature. The reaction mixture is filtered through Cellite, the white aluminate residue is washed with 400 ml of methylene chloride, and the combined filtrates are evaporated in vacuo. The residue is chromatographed on silica gel (hexane/ethyl acetate 1:2). After evaporation and drying under a high vacuum, 3.7 g (84%) of the title compound are obtained as a solidifying oil (72% EE). Selective crystallisation of the racemate from hexane (80 ml/1 g of product) allow 2.7 g (61%) of the title compound to be concentrated in the mother liquor in virtually enantiomerically pure form (97% EE).

¹H NMR (400 MHz, C6D6): 1.17 and 1.39 [2s, H3C—C]; 1.54–1.59 [m, 1H]; 1.71–1.90 [m, 5H thereof 1OH]; [2.01–2.10 [m, 1H]; 3.59 and 3.81 [2s broad, HC(1)]; 4.24 [dd, J=1.4, J=5.5, HC(4)]; 4.68 [t,J=5.3, HC(5)]; [α]$_D^{25}$=−47.0 (c=1.0, methanol).

Example A5:

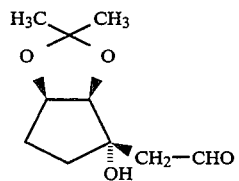

(6)

7.18 g (16.93 mmol) of 1,1,1-tris(acetyloxy)- 1,1-dihydro- 1,2-benziodoxol-3(1H)-one ("Dess-Martin reagent") are introduced into 68 ml of methylene chloride (0.25M solution), and 2.74 g (13.55 mmol) of the compound 5 in 54 ml of methylene chloride (0.25M solution) are added in the course of 5 minutes under an argon atmosphere at room temperature. After the milky-white reaction solution has been stirred for 2 hours, it is poured into a mixture of 50 ml of aqueous Na2S2O3 (20%), 150 ml of saturated aqueous NaHCO3 and 150 ml of diethyl ether. The mixture is stirred for 10 minutes, and the organic phase is then separated off. The aqueous phase is extracted with three times 300 ml of diethyl ether. The combined organic phases are dried over MgSO4, filtered and evaporated in vacuo. The residue is taken up in a little ethyl acetate and filtered through silica gel (ethyl acetate). Bulb-tube distillation under a high vacuum (0.026 bar, 72°–75° C.) gives 1.78 g (66%) of the title compound as a colourless oil.

¹H NMR (300 MHz, C6D6): 1.09 and 1.33 [2s, H3C—C]; 1.51–1.62 [m, 2H]; 1.70–1.77 [m, 1H]; 1.85–1.98 [m, 1H]; 2.23 [dd, J=0.9, J=18.0 HC(2)]; 2.55 [dd, J=1.0, J=18.0 HC(2)]; 2.70 [s broad, OH]; 4.18 [dd, J=1.3, J=5.5 HC(4)]; 4.52 [t,J=5.2 HC(5)]; 9.33 [t,J=1.0 CHO].

Example A6:

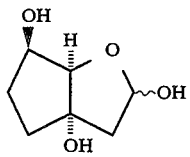

(7a)

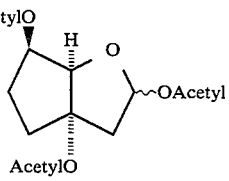

(7b)

a) 1.64 g (8.19 mmol) of the compound 6 dissolved in 40 ml of water and 3.3 g of ion exchanger resin Amberlite IR-120 are stirred for 90 minutes at 55° C. The solution is filtered, and the ion exchanger washed with a little water. The pH of the filtrate is brought to 8.0 using saturated aqueous NaHCO3 solution. The solvent is evaporated in vacuo to a volume of 2 ml, and the residue is taken up in 20 ml of pyridine and evaporated to dryness. Compound 7a, which is obtained as a yellowish oil, is used directly in step b.

b) The yellowish oil is taken up in 25 ml of pyridine, and 5.4 ml (57.13 mmol) of acetic anhydride and 250 mg (2.05 mmol) of 4-dimethylaminopyridine are added at 0° C. After the reaction mixture has been stirred for 3 hours at room temperature, it is again cooled to 0° C., and the reaction is stopped by an addition of 100 ml of saturated aqueous NaHCO3. The mixture is extracted with three times 150 ml of methylene chloride, and the organic phase is separated off, dried over MgSO4, filtered and evaporated to dryness in vacuo. The residue is taken up in twice 100 ml of toluene and evaporated to dryness. The yellowish-brown oil is chromatographed on silica gel (hexane/ethyl acetate 2:1 ), and, after the solvent has been removed and the residue has been dried under a high vacuum (2 days), 2.19 g (93%) of the title compound (7b) are obtained as a slightly yellowish oil which still contains a small amount of ethyl acetate.

¹H NMR (400 MHz, CDCl3): 6.40 [d, J=5.0, 0.5H, HC(1)]; 6.34 [dd, J=2.2, J=5.3, 0.5H HC(1)]; 5.10–5.05 [m, 0.5H, HC(5)]; 5.03–4.97 [m, 0.5H, HC(5)]; 4.79 [d, J=5.3, 0.5H, HC(4)]; 4.73 [d, J=5.8, 0.5H, HC(4)]; 2.67–1.73 [signal cluster 15H, inter alia 2.09, 2.08, 2.063, 2.061, 2.05, 2.04 6s, H3C—CO].

B) PREPARATION OF NUCLEOSIDES

Example B 1:

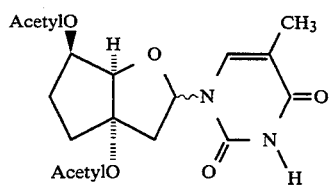
(8)

1.25 g (9.91 mmol) of thymine are suspended under an argon atmosphere in 100 ml of acetonitrile, and 1.65 ml (7.91 mmol) of hexamethyldisilazane, 1.0 ml (7.89 mmol) of trimethylchlorosilane and 1.39 ml (11.83 mmol) of $SnCl_4$ are added in succession at 0° C. 2.83 g (9.89 mmol) of the compound 7(b) dissolved in 20 ml of acetonitrile, are now added to the suspension in the course of 5 minutes, the ice-bath is removed, and the solution, which has turned clear, is stirred for 35 minutes at room temperature and for 35 minutes at 50° C. The solution, which has cooled to room temperature, is poured into 300 ml of saturated aqueous $NaHCO_3$-solution, and the mixture is extracted with twice 300 ml of ethyl acetate. The organic phase is filtered through cotton wool, and the solvent is removed in vacuo. Drying under a high vacuum gives a brownish foam which is chromatographed on silica gel (hexane/ethyl acetate 1:3). After the solvent has been removed in vacuo and the product has been dried under a high vacuum, 2.55 g (73%) of the title compound is obtained as a colourless foam (anomer mixture $\alpha:\beta = 1:2$).

$^1$H NMR (200 MHz, $CDCl_3$): 8.57 [s, broad, 1H, HN]; 7.31, 7.28 [2s, 1H, HC(6)]; 6.30–6.18 [m, 1H, HC(1')]; 5.19–5.00 [m, 1H, HC(5')]; 4.91 [d, J=5.0, 0.4H, HC(4')];4.63 [d, J=6, 0.6H, HC(4')]; 2.96 [dd, J=15.0, 0.6H, HC(2')]; 2.79 [dd, J=7, J=15, 0.4H, HC(2')]; 2.55–1.50 [signal cluster 14H, inter alia 2.13, 2.09, 2.05, 1.95 4s, $H_3C$].

Example B2:

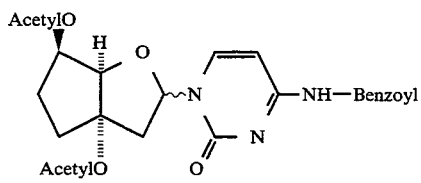
(9)

3.1 ml (12.5 mmol) of N,O-bis-trimethylsilylacetamide are added at room temperature (RT) to a suspension of 1.345 g (6.25 mmol) of N-4-benzoylcytosine in 50 mol of acetonitrile. After 45 minutes, 1.431 g (5 mmol) of the compound 7(b) dissolved in 25 ml of acetonitrile, and 1.91 ml (16.2 mmol) of tin tetrachloride are added in succession to the reaction mixture, which has turned homogeneous. After the reaction mixture has been stirred at room temperature for 50 minutes, it is taken up in 200 ml of methylene chloride and extracted twice with 200 ml of saturated $NaHCO_3$ solution and with twice 200 ml of saturated NaCl solution, the aqueous phases additionally being extracted with twice 200 ml of methylene chloride. The combined organic phases are dried over $MgSO_4$ and concentrated, and the residue is chromatographed on silica gel using methylene chloride/methanol 30:1. In this way, precipitation from 400 ml of pentane and drying under a high vacuum (HV) overnight give 1.99 g (90%) of the title compound as an approximately 1:1 anomer mixture in the form of a slightly brownish powder.

$^1$H NMR (400 MHz, $CDCl_3$): i.a. 8.71 (s, broad,/1H/NH); 8.14, 7.97 (2d, J=7.5,/1H/H—C6); 6.26–6.21 (m/1H/H—C1'); 5.16 (dt, $J_d$=6.9, $J_t$=5.9/0.5H/H—C5'); 5.08 (dt, $J_d$=9.8, $J_t$=5.8/0.5H/H—C(5'); 5.07 (d, J=5.8/0.5H/H—C4'); 4.78 (d, J=5.7/0.5H/H—C4');3.33 (dd, J=5.5, 14.9/0.5H/H—C2'); 2.89 (dd, J=6.6, 15.2/0.5H/H—C2'); 2.72 (dd, J=3.8, 15.2/0.5H/H—C2'); 2.13, 2.12, 2.08, 1.95 (4s/6H/$CH_3CO$).

Example B 3:

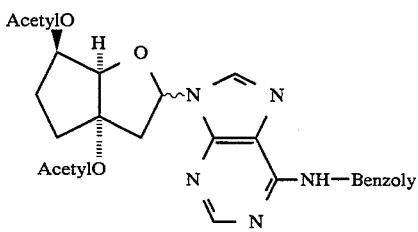
(10)

3.86 g (16.1 mmol) of N-6-benzoyladenine are suspended in 20 ml of acetonitrile, and 5.86 ml (32.3 mmol) of N,O-bis-trimethylsilylacetamide are added. After the reaction mixture has been stirred for 30 minutes at room temperature, a solution of 2.31 g (8.1 mmol) of the compound 7(b) in 15 ml of acetonitrile followed by 200 μl of trimethylsilyl trifluoromethanesulfonate are added to the reaction mixture, which has turned homogeneous. After a reaction time of 2 hours at reflux temperature, the mixture is allowed to cool to room temperature, and stirring is continued for 3 hours. The deep brown reaction solution is subsequently poured into a mixture of 100 ml of saturated NaCl solution and 100 ml saturated $NaHCO_3$ solution and extracted with twice 200 ml of methylene chloride. The combined organic phases are dried over $MgSO_4$ and evaporated. The residue is dissolved in a small amount of ethyl acetate, the solution is filtered, and the filtrate is chromatographed on silica geusing ethyl acetate. The product-containing fractions are combined and freed from solvent, and the resulting residue is dried under a high vacuum (1 h) to give a slightly yellowish foam. 2.94 g (78%) of the title compound remain as an anomer mixture in a ratio of $\alpha:\beta=3:2$. $^1$H NMR (400 MHz, $CDCl_3$):i.a. 8.79, 8.78, 8.25, 8.24 (4s/2H/H—C(2.8); 6.54 (dd, J=3.5, 6.7/0.6H/H—C1'), 6.48 (dd, J=5.8, 9.0/0.4H/H—C(1'); 5.17 (dt,$J_d$=8.4, $J_t$=5.8/0.6H/H—C5'), 5.05 (dt, $J_d$=9.7, $J_t$=6.2/0.4H/H—C5'); 4.98 (d, J=5.3/0.6H/H—C4'); 4.77 (d, J=5.4/0.4H/H—C4'); 3.32 (dd, J=3.5, 15.0/0.6H/H—C2'), 3.14 (dd J=5.8, 14.6/0.4H/H—C2'); 2.91 (dd, J=6.8, 15.1/0.6H/H—C2'); 2.84 (dd, J=8.9, 14.6/0.4H/H—C2'); 2.13, 2.11, 2.04, 1.94 (4s/6H/$CH_3$—CO).

Example B3a:

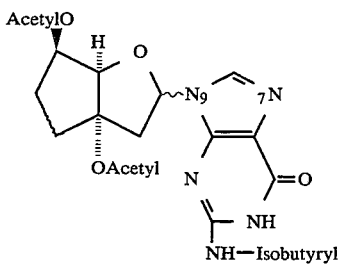

4.69 g (21.2 mmol) of N₂-isobutyroylguanine are suspended under argon in 150 ml of absolute acetonitrile, and 19 ml (76.3 mmol) of N,O-bis(trimethylsilyl)acetamide are added. After the mixture has been stirred for 1 hour at room temperature and for 30 minutes at 40° C., a solution of 3.03 g (10.6 mmol) of the compound 7b in 15 ml of absolute acetonitrile followed by 4.2 ml (5.2 g, 23.3 mmol) of trimethylsilyl trifluoromethylsulfonate are added to the homogeneous mixture. After a reaction time of 16 hours at RT and 6 hours at 40° C., the reaction solution is concentrated and the resulting oil is taken up in 250 ml of methylene chloride, and the mixture is extracted using 2×250 ml of saturated NaHCO₃ solution. The aqueous phases are reextracted using 3×250 ml of methylene chloride. Concentration of the combined organic phases which have been dried over MgSO₄ gives a brown foam which is chromatographed first on 300 g, and then another 2 times on 250 g, of silica gel 60 (methylene chloride: MeOH 39:1 ) to bring about a separation of the diastereomeric reaction products. 2.13 g (45%) of the title compound are obtained as an anomer mixture in a ratio of α:β8:5, and 1.75 g (37%) of the N7 nucleosides, which are isomeric with the title compound, equally as an anomer mixture in the ratio of α:β3:2.

¹H NMR (400 MHz, CDCl₃) of the title compound: 1.23–1.28 (m, 6H, H₃C(isobut)); 1.82–2.03, 2.18–2.28, 2.31–2.41 (m, 4H, H—C(6'), H—C(7')); 1.98, 2.06 (2s, 2.3H, 2 H₃C—CO); 2.04, 2.10 (2s, 2.7H, 2 H₃C—CO); 2.45 (dd, J=9.1, 14.6, 0.55H, H—C(2')); 2.70, 2.71 (heptet, J=6.9, 1H, H—C(isobut)); 2.81 (dd, J=7.0, 15.2, 0.45H, H—C(2')); 3.03 (dd, J=5.7, 14.6, 0.55H, H—C(2')); 3.10 (dd, J=3.2, 15.2, 0.45H, H—C(2')); 4.68 (d, J=5.6, 0.45H, H—C(4')); 4.90 (d, J=5.2, 0.55H, H—C(4')); 4.98–5.03 (m, 0.45H, H—C(5')); 4.10–5.15 (m, 0.55H, H—C(5')); 6.20 (dd, J=5.7, 9.0, 0.55H, H—C(1')); 6.26 (dd, J=3.2, 6.9, 0.45H, H—C(1')); 7.86 (s, 0.55H, H—C(8)); 7.90 (s, 0.45H, H—C(8)); 8.87 (s, br, 0.45H, H—N(1)); 8.93 (s, br, 0.55H, H—N(1)); 2.15, 2.20 (2s, br, 1H, H—N(2)).

Example B4:

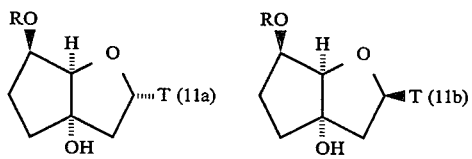

R = t-butyldimethysilyl
T = thymidyl 2.30 g (6.53 mmol) of the compound 8 are dissolved in 260 ml of solvent mixture (tetrahydrofuran (THF)/methanol/H₂O 5:4:1), and 26 ml (52 mmol) of 2N NaOH are added at 0° C. After the mixture has been stiffed at the same temperature for 75 minutes, 3.5 g (65.4 mmol) of NH₄Cl are added, and stirring is continued until a clear solution forms. The solvent is removed in vacuo, the residue is taken up in 200 ml of methanol, and the mixture is adsorbed on 8 g of silica gel and chromatographed on silica gel (methylene chloride/methanol 5:1 ). The solvent is removed in vacuo. The colourless foam is dissolved in a small amount of methanol, 100 ml of pentane are added, and the mixture is evaporated to dryness in vacuo. After drying overnight under a high vacuum, 1.65 g (94%) of the deacetylated product are obtained as a colourless powder. This powder is dissolved in 33 ml of pyridine with gentle heating, and 1.84 ml (8.01 mmol) of t-butyldimethylsilyl triflate are then added at 0° C. under an argon atmosphere. Stirring is continued for 45 minutes at this temperature. 100 ml of saturated aqueous NaHCO₃ solution are added to the clear reaction solution, and the mixture is extracted three times using 150 ml portions of ethyl acetate. The solvent is removed in vacuo, and the colourless foam is dried briefly under high vacuum. Chromatography on silica gel (5% of acetone in diethyl ether) gives the two anomers of the title compound: 11 a, 655 mg (28%) and 11 b, 1.47 g (62%). ¹H NMR of 11 a (400 MHz, CDCl₃): i.a. 7.37 [s, 1H, HC(6)]; 6.05 [dd, J=2.5, J=7.8, 1H,HC(1')]; 4.45 [d, J=4.6, 1H,HC(4')]; 4.15 [dd, J=4.2, J=8.6, 1H,HC(5')]; 2.61 [dd, J=7.9, J=14.7, 1H,HC(2')]; 2.49 [d, J=14.5, 1H,HC(2')]; 1.89 [s, 3H, H₃C—C(5)]; 0.91 [s, 9H, H₃C—C]; 0.10, 0.09 [2s, 6H, H₃C—Si]. ¹H NMR of 11 b (400 MHz, CDCl₃): i.a. 7.66 [s, 1H, HC(6)]; 6.39 [dd, J=4.9, J=9.3, 1H,HC(1')]; 4.19 [m, 1H,HC(5')]; 4.08 [d, J=6.0, 1H,HC(4')]; 3.18 [s broad, 1H,OH]; 2.67 [dd, J=5.0, J=13.6, 1H,HC(2')]; 1.92 [s, 3H, H₃C—C(5)]; 0.91 [s, 9H,H₃C—C]; 0.11, 0.09 [2s, 6H, H₃C—Si].

Example B4a:

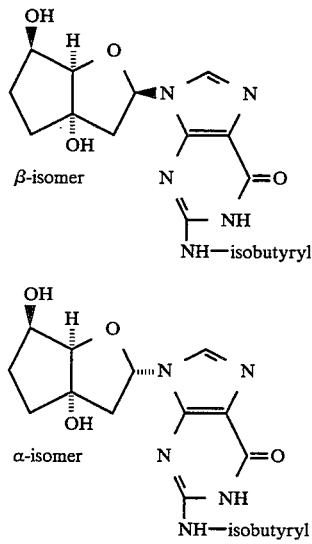

1.13 g (2.53 mmol) of the title compound of Example B3a are dissolved in 250 ml solvent mixture (THF:MeOH:H₂O 5:4:1), and 25 ml (50 mmol) of 2N NaOH are added at 2° C. The mixture is stirred for 25 minutes at the same temperature, and 4 g (75 mmol) of ammonium chloride are then added, and stirring is continued until a clear solution forms. The solvent is stripped off, and the white residue is then dried briefly under a high vacuum and subsequently chromatographed on 150 g of silica gel 60 (methylene chloride:-methanol 10:1) to bring about separation of the anomers. Pure fractions are combined, mixed fractions can be separated by repeated chromatography on silica gel 60. In this manner, 427 mg (47%) of the more apolar β-isomer and 254 mg (28%) of the more polar α-isomer are obtained. In total 681 m g (75 %). $^1$H NMR (400 MHz, CD$_3$OD) of the α-anomer: 1.25 (d, J=6.8, 6H, H$_3$C(isobut)); 1.69–1.80, 2.02–2.11 (2m, 4H, H—C(6'), H—C(7')); 2.65 (dd, J=7.2, 14.4, 1H, H—C(2')); 2.73–3.17 (m, 2H, H—C(2'), H—C(isobut)); 4.11–4.16 (m, 1H, H—C(5')); 4.34 (d, J=5.2, H—C(4')); 6.42 (dd, J=2.8, 7.1, 1H, H—C(1')); 8.38 (s, 1H, H—C(8)). $^1$H NMR (400 MHz, CD$_3$OD) of the β-anomer: 1.22 (d, J=6.9, 6H, H$_3$-C(isobut)); 1.65–1.72, 1.86–1.97, 2.06–2.15 (3m, 4H, H—C(6'), H—C(7')); 2.50 (dd, J=9.7, 13.2, 1H, H—C(2')); 2.57 (dd, J=5.4, 13.3, 1H, H—C(2')); 2.72 (heptet, J=6.9, 1H, H—C(isobut)); 4.09–4.13 (m, 2H, H—C(4'), H—C(5')); 6.32 (dd, J=5.4, 9.6, 1H, H—C(1')); 8.3 (s, 1H, H—C(8)).

Example B5:

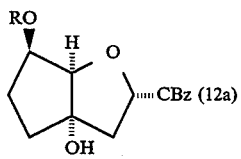

R = t-butyldimethysilyl
CBz = benzoylcytosyl 1.99 g (4.5 mmol) of the compound 9 are dissolved in 400 ml of THF/methanol/water 5:4:1, and 40 ml of 2N aqueous NaOH are added at 0° C. The mixture is stirred for 20 minutes at 0° C., and 6 g (112 mmol) of ammonium chloride are then added, the reaction mixture is subsequently evaporated and the residue is chromatographed on silica gel using methylene chloride/methanol 10:1. The product-containing fractions are combined and concentrated, the resulting residue (1.35 g) is dissolved in 26 ml of pyridine, and 1.11 ml (4.86 mmol) of t-butyldimethylsilyl trifluoromethanesulfonate are added at 0° C. After 30 minutes, the reaction mixture is taken up in 200 ml of saturated aqueous NaHCO$_3$solution, and the mixture is extracted with three times 200 ml of ethyl acetate. The combined organic phases are dried over MgSO4 and concentrated and the residue is chromatographed on silica gel using ethyl acetate. According to the elution sequence, after drying overnight, 865 mg (41%) of the compound 12b are obtained as a colourless crystallisate and 677 mg (32%) of 12a are obtained as a colourless foam in this manner. $^1$H NMR of 12a (400 MHz, CDCl$_3$): i.a. 7.95 (d, J=7.4/1H/H—C6); 6.06 (dd, J=3.0, 5.7/1H/H—C1'); 4.53 (d, J=4.6/1H/H—C4'); 4.16 (dd, J=4.0, 8.5/1H/H—C5'); 2.67–2.65 (m/2H/H—C2'). $^1$H NMR of 12b (400 MHz, CDCl$_3$): i.a. 8.59 (d, J=7.5/1H/H—C6); 6.47 (dd, J=5.4, 8.5/1H/H—C1'); 4.24 (d, J=5.4/1H/H—C4'); 4.24–4.16 (m/1H/H—C5'); 3.10 (dd, J=5.4, 14.0/1H/H—C2'); 1.77 (dd, J=8.5, 14.0/1H/H—C2').

Example B6:

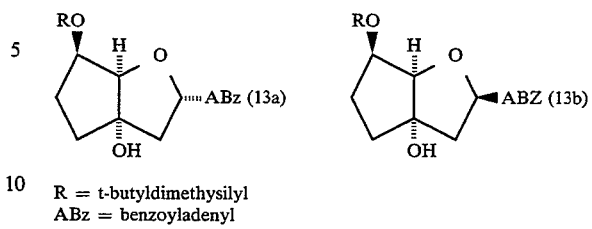

R = t-butyldimethysilyl
ABz = benzoyladenyl 3.36 g (7.24 mmol) of the compound 10 are dissolved in 289 ml of a mixture of THF/methanol/water 5:4:1, and 28.9 ml of 2N NaOH solution are added at 0° C. The reaction mixture is stirred for 30 minutes, 3.6 g (67 mmol) of ammonium chloride are then added and the ice-bath is removed. After a homogeneous solution has formed, the reaction mixture is concentrated, the residue is dissolved in 50 ml of methanol, and the mixture is adsorbed on 5 g of silica gel. Chromatography on silica gel using methylene chloride/methanol 9:1 gives, after brief drying, 1.98 g of the deacetylated product, which is subsequently dissolved in 20 ml of pyridine, and 1.43 ml (6.24 mmol) of t-butyldimethylsilyl trifluoromethanesulfonate are added at 0° C. After a reaction time of 30 minutes, the mixture is poured into 100 ml of aqueous NaHCO$_3$ solution and extracted with twice 200 ml of ether. The combined organic phases are dried over MgSO$_4$ and evaporated. The crude product (2.3 g) is chromatographed on silica gel using diethyl ether (saturated with water)/acetone 83:17, the isomer 13a being eluted first, followed by the isomer 13b. Pure fractions are combined and evaporated, and mixed fractions are chromatographed analogously one more time. In this manner, 1.452 g (57%) of 13a and 0.864 g (33%) of 13b are obtained after drying overnight, in each case in the form of a white foam. $^1$H NMR of 13a (400 MHz, CDCl$_3$): i.a. 8.79, 8.07 (2s/2H/H—C2.8); 6.34 (dd, J=3.8, 7.3/1H/H—C1'); 4.39 (d, J=4.8/1H/H—C4'); 4.18 (dt, J$_d$=6.1, J$_t$=4.8(1H/H—C5'); 2.92–2.82 (m/2H/H—C2'), 0.92 (s/9H/3CH$_3$—C); 0.107, 0.102 (2s/6H/2CH$_3$—Si). $^1$H NMR of 13b (400 MHz, CDCl$_3$): i.a. 8.79, 8.47 (2s/2H/H—C2.8); 6.57 (dd, J=5.3 9.0/1H/H—C1 '); 4.23–4.18 (m/2H/H—C4', 5'); 3.07 (s,broad/1H/OH); 2.84 (dd, J=5.4, 13.5/1H/H—C2'); 2.37 (dd, J=9.1, 13.6/1H/H—C2'); 0.88 (s/9H/3CH$_3$—C); 0.10, 0.06 (2s/6H/2CH$_3$—Si).

Example B7:

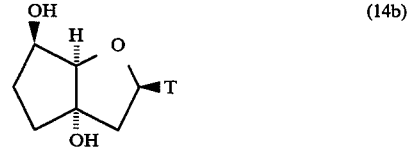

1.76 g (5.58 mmol) of tetrabutylammonium fluoride (TBAF). 3H$_2$O are added at room temperature to a solution of 1.07 g (2.80 mmol) of the compound 11 b in 20 ml of tetrahydrofuran, and the mixture is allowed to stand for 4 days. The reaction mixture is adsorbed on 10 g of silica gel and chromatographed on silica gel (methylene chloride/methanol 6:1 ). Crystallisation of the product (methanol/diethyl ether 4:1/pentane:isothermal distillation) gives 521 mg (69%) of the title compound as colourless crystals.

¹H NMR (400 MHz, D₂O): i.a. 7.67, [s, 1H,HC(6)]; 6.24 [dd, J=5.2, J=10.1, 1H,HC(1')]; 4.19 [dt, Jt=5.6, Jd=9.4, 1H, HC(5')]; 4.09 [d, J=5.3, 1H,HC(4')]; 2.49 [dd, J=5.2, J=1.41, 1H,HC(2')]; 2.15 [dd, 10.2, J=14.1, 1H,HC(2')]; 1.89 [s, 3H,H₃C—C(5)].

Example B8:

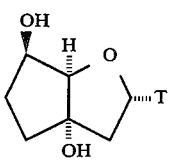
(14a)

Analogously to Example B7, 638 mg (1.67 mmol) of the compound 11 a give 345 mg (77%) of the title compound as colourless crystals after chromatography on silica gel (methylene chloride/methanol 6:1 ) and crystallisation from (methanol/diethyl ether 4:1/pentane:isothermal distillation).

¹H NMR (300 MHz, D₂O): i.a. 7.69 [s, 1H,HC(6)]; 6.15 [dd, J=4.3, J=7.0, 1H,HC(1')]; 4.37 [d, J=5.3, 1H,HC(4')]; 4.17–4.10 [m, 1H,HC(5')]; 2.57 [dd, J=7.0, J=14.7, 1H,HC(2')]; 2.38 [dd, J=4.3, J=14.7, 1H,HC(2')]; 1.84 [s, 3H,H₃C—C(5)].

Example B9:

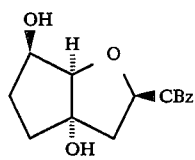
(15b)

992 mg (2.77 mmol) of the compound 12b are dissolved in 27 ml of THF, and 1.75 g (5.5 mmol) of tetrabutylammonium fluoride trihydrate are added. After a reaction time of 84 hours at room temperature, the mixture is concentrated and the residue is chromatographed on silica gel using methylene chloride/ethanol 10:1. The combined product-containing fractions are concentrated and the residue (670 mg) is suspended in 6 ml of water at 60° C. The suspension is allowed to stand at room temperature for a few hours and then filtered, and the fine white needles of the title compound are dried for a few hours at 40° C. under a high vacuum. 488 mg (66%) of the title compound are obtained.

¹H NMR (400 MHz, d6-DMSO): i.a. 8.59 (d, J=7.5/1H/H—C6); 6.18 (dd, J=5.3, 9.2/1H/H—C1 '); 4.01–3.95 (m/2H/H—C4', 5'), 2.54–2.49 (m/H—C2'+solvent); 1.82 (dd, J=9.2, 13.3/1H/H—C2').

Example B 1 0:

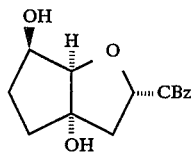
(15a)

The procedure of Example B9 is followed analogously using 806 mg (2.25 mmol) of the compound 12a. After chromatography on silica gel using methylene chloride/methanol 10:1 followed by crystallisation from methanol/ether/pentane, 398 mg (65%) of the title compound are obtained in the form of white needles arranged in the shape of a star.

¹H NMR (400 MHz, d6-DMSO): i.a. 8.26 (d, J=7.4/1H/H—C6); 6.14 (dd, J=2.9, 7.0/1H/H—C1'); 4.37 (d, J=5.2/1H/H—C4'); 3.96 (dt, J_d=11.2, J_t=5.9/1H/H—C5'); 2.51–2.46 (m/H—C'''+solvent); 2.23 (dd, J=2.9, 14.1/1H/H—C2').

Example B 11:

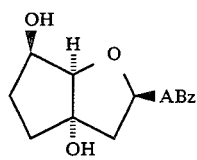
(16b)

852 mg (1.72 mmol) of the compound 13b are dissolved in 20 ml of THF, and 651 mg (2.1 mmol) of tetrabutylammonium fluoride trihydrate are added. After a reaction time of 12 hours at 50° C., 500 mg (9.3 mmol) of ammonium chloride are added, and the reaction mixture is concentrated after a further 30 minutes. The residue is chromatographed on silica gel using methylene chloride/methanol 9:1, and the product fractions (which are still contaminated with tetrabutylammonium salts) are evaporated. The residue is crystallised from 10 ml of water and the product is dried for 15 hours under a high vacuum, after which 530 mg (81%) of the title compound are obtained in the form of colourless needles.

¹H NMR (300 MHz, CD₃OD): 8.73, 8.71 (2s/2H/H—C2.8); 8.09 (d broad/2H/H-aromatic); 7.70–7.54 (m/3H/H-aromatic); 6.58 (dd, J=5.0, 9.0/1H/H—C1'); 4.22–4.10 (m/2H/HC—4', 5'); 2.72 (dd, J=9.0, 13.0/1H/H—C2'); 2.66 (dd, J=5.0, 13.0/1H/H—C2'); 2.20–1.65 (m/4H/H—C6', 7').

Example B 12:

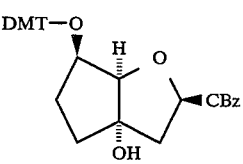
(17)

2.22 g (4.91 mmol) of 4,4'-dimethoxytriphenylmethyl trifluoromethanesulfonate (DMT triflate) are added to a suspension of 1.17 g (3.27 mmol) of the compound 15b in 24 ml of lutidine and 24 ml of methylene chloride. The solution is stirred for 4 hours and then poured into 250 ml of saturated aqueous NaHCO₃ solution, and the mixture is extracted with three times 250 ml of methylene chloride. The organic phases are dried over MgSO₄ and filtered, and the solvent is removed in vacuo. Lutidine is removed under a high vacuum (HV), and the resulting brown foam is subsequently chromatographed on silica gel (triethylamine/ethyl acetate 1:99). 1.96 g (91%) of the title compound are obtained as a virtually colourless foam.

¹H NMR (400 MHz, CDCl₃): i.a. 8.75 [d, J=7.5, 1H,HC(6)]; 6.85 [dd, J=2.0, J=8.9, 4H, H-aromatic (trityl)]; 6.33 [dd, J=5.6, J=8.1, 1H,HC(1')]; 3.98–3.91 [m, 1H,HC(5')]; 3.80 [s, 6H,OCH₃]; 3.69 [d, J=6.4, 1H,HC(4')]; 3.04 [dd, J=5.6, J=14.1, 1H,HC(2')].

Example B 13:

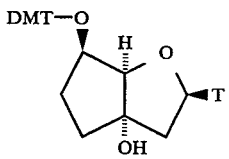

(18)

Analogously to Example B12, 442 mg (4.65 mmol) of the compound 14b give 736 mg (78%) of the title compound after chromatography on silica gel (hexane/ethyl acetate 1:9, 2% of triethylamine) and crystallisation (ethyl acetate/pentane).

$^1$H NMR (200 MHz, CDCl$_3$): i.a. 7.78 [d, J=1.0, 1H,HC(6)]; 6.83 [d, J=9.0, 4H, H-aromatic (trityl)]; 6.29 [dd, J=5.0, J=10.0, 1H,HC(1')]; 3.99-3.87 [m, 1H,HC(5')]; 3.76 [s, 6H,OCH$_3$]; 3.72 [d, J=6.0, HC(4')]; 2.58 [dd, J=5.0, J=13.0, 1H,HC(2')]; 1.75 [d, J=1.0, 3H,H$_3$C—C(5)].

Example B 14:

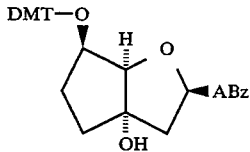

(19)

505 mg (1.32 mmol) of the compound 16b are dissolved in 10 ml of pyridine, and 1.198 g (2.64 mmol) of DMT triflate are added. After 30 minutes, a further 2.0 g (4.4 mmol) of DMT triflate are added. After a total reaction time of 3 hours, the crude mixture is taken up in 100 ml of ethyl acetate and extracted with three times 100 ml of saturated NaHCO$_3$ solution. The aqueous phases are extracted once more using 100 ml of ethyl acetate in each case. The combined organic phases are evaporated and the residue is chromatographed on silica gel. First, apolar by-products are eluted using ethyl acetate, then, using methylene chloride/methanol 9: 1, the desired title compound is eluted which, after concentration and drying overnight under a high vacuum, is obtained in an amount of 770 mg (85%) as a slightly yellowish foam.

$^1$H NMR (200 MHz, CDCl$_3$): i.a. 8.80,8.51 (2s/2H/HC-2.8); 6.81 (d br/4H/H-aromatic (trityl)); 6.41 [dd, J=4.0,9.0/1H/H—C1'); 4.92 (dt, J$_d$=10.0, J$_t$=10.0, J$_t$=5.0/1H/H—C5'); 3.76 (s/6H/O—CH$_3$); 3.69 (d, J=5.0/1H/H—C4'); 2.79 (dd, J=4.0, 14.0/1H/H—C2'); 2.35 (dd, J=9.0, 14.0/1H/H—C2').

Example B 14a:

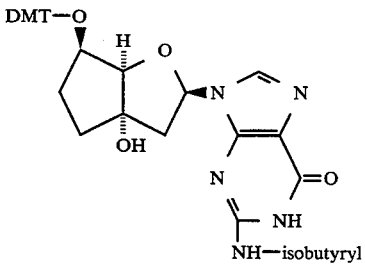

221 mg (608 μmol) of the compound of Example 4a (β-isomer) are dissolved in 2 ml of absolute pyridine and 413 mg (912 μmol) of DMT triflate are added, with stirring. Further portions of 137 mg (304 μmol) of DMT triflate are added after 2 and 4 hours. After 6.5 hours, the mixture is taken up in 20 ml of methylene chloride and extracted by a succession of 15 ml of saturated NaHCO$_3$ solution, 15 ml of aqueous citric acid solution (10%) and 15 ml of saturated NaHCO$_3$ solution. Each of the aqueous phases is reextracted with 10 ml of methylene chloride. The combined organic phases are dried over MgSO$_4$ and concentrated, and the yellow foam obtained is chromatographed on 40 g of silica gel 60 (methylene chloride:methanol 20:1, 2% of triethylamine). Subsequent precipitation from 120 ml of diethyl ether at RT gives 313 mg (77%) of the title compound as a white powder.

$^1$H NMR (400 MHz, CDCl$_3$): 1.10-1.25, 1.68-1.70 (2m, 9H, H$_3$C(isobut), H—C(6'), H—C(7')); 2.02 (dd, J=8.5, 13.0, 1H, H—C(2')); 2.81-2.88 (m, 1H, H—C(isobut)); 3.69, 3.70 (2s, 6H, H$_3$C—O(DMT)); 3.88-3.90 (m, 2H, H—C(4'), H—C(5')); 4.40 (s, br, 1H, HO—C(3')); 6.02-6.06 (m, 1H, H—C(1')); 6.73 (dd, J=7.6, 8.9, 4H, H—C(ar)); 7.11 (t, J=7.3, 1H, H—C(ar)); 7.16-7.20 (m, 2H, H—C(ar)); 7.33-7.36 (m, 4H, H—C(ar)); 7.46 (d, J=7.3, 2H, H—C(ar)); 8.16 (s, 1H, H—C(8)); 10.9 (s, br, 1H, H—N(2)); 12.3 (s, br, 1H, H—N(1)).

Example 15:

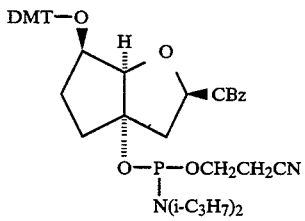

(20)

395 mg (0.6 mmol) of the compound 17 are dissolved in 5 ml of THF under argon, and 410 μl (2.4 mmol) of N,N-diisopropylethylamine as well as 270 μl (1.2 mmol) of 2-cyanoethyl-N,N-diisopropylchlorophosphoramidite are added. The reaction mixture is stirred for 2 hours, 50 ml of ethyl acetate are then added, and the mixture is extracted with twice 20 ml of saturated aqueous NaHCO$_3$ solution. The organic phase is dried over MgSO$_4$ and filtered and the solvent is removed in vacuo. The yellow foam which has been dried under a high vacuum is chromatographed on silica gel (hexane/ethyl acetate 1:2, 1.5% of triethylamine). The resulting yellowish foam is reprecipitated twice (methylene chloride/pentane) and 374 mg (73%) of the title compound are isolated as a colourless powder.

$^1$H NMR (400 MHz, CDCl$_3$): i.a. 8.75 [d, J=7.4, 1H,HC(6)]; 6.86 (dd, J=1.9, J=8.6, 4H,H-aromatic (trityl)]; 6.21-6.15 [m, 1H,HC(1')]; 3.82, 3.81 [2s, 6H, OCH$_3$]; 2.63 [t, J=6.4, 1H, —H$_2$C—CN]; 2.55 [q, J=6.2, 1H, —H$_2$C—CN]; 1.15-1.11 [m, 12H, CH(CH$_3$)$_2$].

Example B 16:

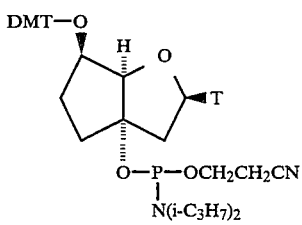

(21)

Analogously to Example B 15, 108 mg (0.189 mmol) of the compound 18 give, after chromatography on silica gel (hexane/ethyl acetate/triethylamine 20:10:4), 91 mg (62%) of the title compound as a white foam.

$^1$H NMR (200 MHz, CDCl$_3$): i.a. 7.79, 7.78 [2d, J=1.0, 1H,HC(6)]; 6.82 (d broad, J=8.0, H-aromatic (trityl)]; 6.33–6.20 [m, 1H,HC(1')]; 3.78, 3.77 [2s, 6H, OCH$_3$]; 2.62, 2.56 [2t, J=7.0, 2H, —H$_2$C—CN]; 1.73, 1.68 [2d, J=1.0, H$_3$C—C(5)]; 1.19–1.09 [m, 12H, CH(CH$_3$)$_2$].

Example B 17:

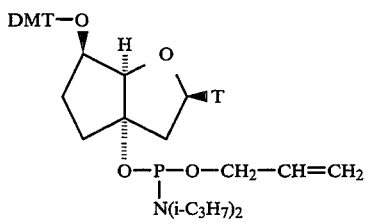

(22)

Analogously to Example B 15, 200 mg (0.35 mmol) of the compound 18 give, after reaction with allyloxychloro-N,N-diisopropylaminophosphite in CH$_2$Cl$_2$ and after chromatography on silica gel (hexane/ethyl acetate 1:2), 236 mg (89%) of the title compound as a colourless foam.

$^1$H NMR (200 MHz, CDCl$_3$): i.a. 7.82 [s broad, 1H,HC(6)]; 6.83 [d, J=9.0, 4H, H-aromatic (trityl)]; 6.43–6.22 [m, 1H,HC(1')]; 5.99–5.75, 5.31–5.05 [2m, 3H, H allyl]; 3.79, 3.78 [2s, 6H,OCH$_3$]; 1.73, 1.71 [2d, J=1.0, H$_3$C—C(5)]; 1.25–1.05 [m, 12H, CH(CH$_3$)$_2$].

Example B 18:

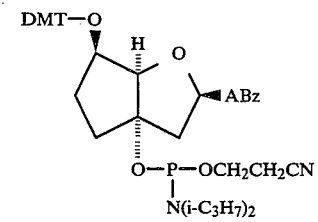

(23)

341 mg (0.5 mmol) of the compound 19 are dissolved in 4 ml of methylene chloride and 342 µl (2.0 mmol) of ethyldiisopropylamine and 223 µl (1.0 mmol) of 2-cyanoethyl N,N-diisopropylchlorophosphoramidite are added in succession at room temperature. After a reaction time of 1 hour, the crude mixture is taken up in 50 ml of ethyl acetate, and the mixture is extracted twice with 50 ml of NaHCO$_3$ solution. The organic phase is filtered through cotton wool and concentrated and the residue is chromatographed on silica gel using ethyl acetate. The product is dried overnight under a high vacuum, and 348 mg (79%) of the title compound result in the form of a pale yellow foam.

$^1$H NMR (200 MHz, CDCl$_3$): i.a. 8.82, 8.81, 8.51, 8.50 [4s/2H/H—C2', 8']; 6.82 (m(doubletoid/4H/H-aromatic (trityl)); 6.49–6.35 (m/1H/H—C1'); 3.75, 3.74, (2s/6H/2O—CH$_3$); 2.61, 2.58 (2t, J=6.0/CH$_2$—CN); 1.23–1.10 (m/12H/CH(CH$_3$)$_2$].

Example B 18a:

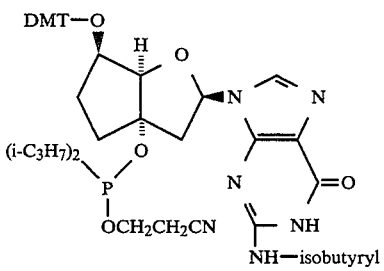

719 mg (1.08 mmol) of the title compound of B 14a are dissolved in 10 ml of absolute THF under argon and 750 µl (4.32 mmol) of diisopropylethylamine and 490 µl (2.16 mmol) of 2-cyanoethyl N,N-diisopropylchlorophosphoramidite are added in succession. The reaction mixture is stirred for 3 hours at room temperature and then taken up in 25 ml of ethyl acetate, the mixture is extracted with 20 ml of saturated NaHCO$_3$ solution and the aqueous phase is reextracted using 15 ml of ethyl acetate. The combined organic phases are dried over MgSO$_4$ and concentrated and the brown residue is filtered through 20 g of silica gel (ethyl acetate). 880 mg (94%) of the title compound are obtained in the form of a virtually colourless foam.

$^1$H NMR (400 MHz, CDCl$_3$): 1.09–1.15 (m, 12H, H$_3$C(isoprop)); 1.21–1.24 (m, 6H, H$_3$C(isobut)); 1.42–1.58, 1.82–1.95 (2m, 4H, H—C(6'), H—C(7')); 2.04 (dd, J=8.8, 13.8, 0.4H, H—C(2')); 2.12 (dd, J=9.1, 14.14, 0.6H, H—C(2')); 2.52–2.59 (m, 1H, H—C(isobut) 2.62–2.71 (m, 2H, H$_2$C—CN)); 3.08 (dd, J=5.3, 15.2, 0.6H, H—C(2')); 3.17–3.21 (m, 0.4H, H—C(2')); 3.48 (d, J=6.1; 0.4H, H—C(4')); 3.50–3.61 (m, 2H, N—CH(CH$_3$)$_2$); 3.62–3.69 (m, 1H, H—C(5')); 3.79, 3.79 (2s; H$_3$C—O(DMT)); 3.81–3.89 (m, 2H, H$_2$C—O); 3.92 (dd, J=2.9, 6.0, 0.6H, H—C(4')); 6.05 (dd, J=5.2, 8.7, 0.4H,H—C(1')); 6.17 (dd, J=5.4, 9.0, 0.6H, H—C(1')); 6.80–7.00 (m, 4H, H—C(ar)); 7.18–7.23 (m, 1H, H—C(ar)); 7.27–7.31 (m, 2H, H—C(ar)); 7.39–7.44 (m, 4H, H—C(ar)); 7.51–7.55 (5m, 13H, H—C(ar)); 8.14 (s, 0.6H, H—C(8)); 8.18 (s, 0.4H, H—C(8)); 8.97 (s, 0.6H, H—N(2)); 9.20 (s, 0.4H, H—N(2)); 11.95 (s, br, 1H, H—N(1 )).

C) Preparation of oligonucleotides

Examples C1-C10:

Preparation of the solid-phase-bound nucleosides: The tritylated nucleosides 17, 18 and 19 are attached to long-chain alkylamino-CPG SIGMA ®by means of a succinic acid linker, following the customary methods [Oligonucleotide synthesis a practical approach M. J. Gait; IRL Press 1984 (Oxford-Washington, D.C.)]. Loading densities of 20–30 µmol/g of carrier are achieved (trityl assay).

Oligonucleotide synthesis: The oligonucleotide synthesis is effected using a DNA synthesiser (Pharmacia. LKB Gene Assembler ®Plus) following the standard protocols of the manufacturer (Owners Manual Gene Assembler ®Plus). The following steps in the synthesis cycle are modified:

Detritylation step: 45–60 seconds

Coupling step: 15–20 equivalents of phosphoramidite (0.1 M in CH$_3$CN), 180 equivalents of tetrazole, 6 minutes.

According to the trityl assay, coupling yields of more than 97% per step are generally achieved. In the case of the cyanoethoxy-phosphoramidites, the sequences are deprotected by customary methods and detached from the carder [Oligonucleotide synthesis a practical approach M. J. Gait; IRL Press 1984 (Oxford-Washington, D.C.)]. In the case of the allyloxy-phosphoramidites, deprotection and detaching from the carrier material is as described by Y. Hayakawa, S. Wakabayashi, H. Karo and R. Noyori J. Am. Chem. Soc. 1990, 112, 1691.

Purification of the oligonucleotide sequences: The oligonucleotides are separated by means of HPLC in system 1 and, after demineralisation, injected into system 2 for control purposes. System 1: Precolumn: Nucleogen guard column, 30×4.0 mm, ID (Macherey Nagel); Column: Nucleogen DEAE 60-7, 125×4.0 mm (Macherey Nagel) A: 20 mM KH$_2$PO$_4$ in H$_2$O/CH$_3$CN 4.1, pH 6.0 B: 1M KCl in buffer A, pH 6.0 Flow rate 1 ml/min.

System 2: Precolumn: Rp-8 Newguard, 15×3.2 mm, 7 μm (Brownlee Labs); Column: Aquapore Rp-300, 220×4.6 mm, 7 μm (Brownlee Labs) A: 0.1M triethylammonium acetate (TEAOAc) in H$_2$O, pH 7.0 B: 0.1M TEAOAc in H$_2$O/CH$_3$CN 1:4, pH 7.0 Flow rate 1 ml/min. The detection is by means of UV spectrometry at 260 nm.

Example C1

An oligonucleotide having 6 monomer units is prepared from compounds (17) and (20).

Example C2

An oligonucleotide having 10 monomer units is prepared from compounds (18) and (22).

Example C3

An oligonucleotide having 10 monomer units is prepared from compounds (19) and (23).

Example C4

An oligonucleotide having 6 monomer units is prepared from the compounds of Example B 14a and 18a.

Example C5

An oligonucleotide having 9 monomer units of the sequence 5'-GGA TGG GAG-3' is prepared from the compounds of Example B 14a and B 18a as well as the compounds 22 and 23.

Example C6

An oligonucleotide having 9 monomer units of the sequence 5'-CTC CCA TCC-3' is prepared from compounds 17, 20, 22 and 23.

Example C7

A chimeric oligonucleotide having 18 monomer units of the sequence 5'-CTC GTA CC*C TTC CGG TCC-3' is prepared from compound 20 and conventional 2'-cyanoethyl diisopropylaminophosphoramidite units of the natural 2'-deoxyribonucleosides as well as suitably nucleoside-modified solid phase, manufactured by Pharmacia ®, *C indicating the position of the nucleoside according to compound 20.

Example C8

A chimaeric oligonucleotide having 18 monomer units of the sequence 5'-CTC GTA CC*A TTC CGG TCC-3' is prepared from compound 23 and conventional 2'-cyanoethyl diisopropylaminophosphoramidite units of the natural 2'-deoxyribonucleosides as well as suitably nucleoside-modified solid phase, manufactured by Pharmacia ®, *A indicating the position of the nucleoside according to compound 23.

Example C9

A chimaeric oligonucleotide having 18 monomer units of the sequence 5'-CTC GTA CC*T TTC CGG TCC-3' is prepared from compound 22 and conventional 2'-cyanoethyl diisopropylaminophosphoramidite units of the natural 2'-deoxyribonucleosides as well as suitably nucleoside-modified solid phase, manufactured by Pharmacia ®, *T indicating the position of the nucleoside according to compound 22.

Example C10

A chimaeric oligonucleotide having 18 monomer units of the sequence 5'-CGA CTA TGC AA*C*C*C*C-3' is prepared from compound 20 and conventional 2'-cyanoethyl diisopropylaminophosphoramidite units of the natural 2'-deoxyribonucleosides as well as suitably nucleoside-modified solid phase, manufactured by Pharmacia ®, *C indicating the positions of the nucleosides according to compound 20.

| | Separation of the oligonucleotides: | |
|---|---|---|
| Example | System 1 | System 2 |
| C1 | 14 minutes | 31 minutes |
| | 30–45% B in 23 minutes | 0–20% B in 40 minutes |
| C2 | 31 minutes | 21 minutes |
| | 20–50% B in 40 minutes | 15–22% B in 30 minutes |
| C3* | — | 21.7 minutes |
| | | 10–17% B in 30 minutes |
| C4** | | 7.7 minutes 55% B isocratic |
| C5* | — | 9.0 minutes |
| | | 17–20% B in 30 minutes |
| C6* | 13.2 minutes | 23.2 minutes |
| | 42–52% B in 30 minutes | 0–35% B in 35 minutes |
| C7 | 26.5 minutes | 8.6 minutes |
| | 40–100% B in 30 minutes | 25–35% B in 20 minutes |
| C8 | 25.8 minutes | 8.4 minutes |
| | 40–100% B in 30 minutes | 25–45% B in 20 minutes |
| C9 | 26.0 minutes | 8.4 minutes |
| | 40–100% B in 30 minutes | 25–35% B in 20 minutes |
| C10 | 20.1 minutes | 42.0 minutes |
| | 60–85% B in 25 minutes | 0–25% B in 50 minutes |

*Preparative separation by means of system 2.
**Separation system: column: MonoQ HR5/5 (Phannacia ®)
A: 0.01 M NaOH in H$_2$O
B: 0.01 M NaOH, 1M NaCl in H$_2$O
Flow rate 1 ml/min.
Detection: 260 nm.

D) USE EXAMPLES

Example D 1

Interaction of the oligonucleotides according to Examples C2 and C3 with polynucleotides.

The interaction of the oligonucleotides according to Examples C2 and C3 with the corresponding base-complementary oligomers and polymers of the natural deoxyribonucleosides and ribonucleosides are characterised by recording UV fusion curves and the $T_m$ values calculated therefrom. This standard method is described, for example, by L. A. Marky et at. in Biopolymers, Volume 26, pages 1601 et seq. (1987). A solution of the oligonucleotides according to Examples C2 and C3 and of the corresponding base-complementary natural oligonucleotides, or polynucleotides (see Table 1, c=45 μM), in 10 mM tris-HCl, 0.15 M NaCl, pH=7.0, is prepared and the change in absorbance at 260 nm as a function of the temperature (0° to 70° C.) is recorded. The $T_m$ value is determined from the fusion curves obtained (see Table 1).

TABLE 1

| Complex | $T_m$ value (°C.) |
|---|---|
| C2 · dA-10 | 11.7 |
| C2 · poly dA | 7.0 |
| C2 · poly A | 20.0 |
| C3 · poly U | 45.5 |
| C3 · dT-10 | 25.6 |
| C4 · d(C)$_6$(6,7 μM in duplex) | 16.2 |
| C5 · d(CTC CCA TCC) (5.0 μM in duplex) | 23.9 |
| C6 · d(GGA TGG GAG) (5.0 μM in duplex) | 35.3 |
| C7 · r(GGA CCG GAA GGG UAC GAG) | 67.5* |
| C8 · r(GGA CCG GAA UGG UAC GAG) | 61.2* |
| C9 · r(GGA CCG GAA AGG UAC GAG) | 63.4* |
| C10 · r(GGG GUU GCA UAG UCG) | 59.0* |

*)Duplex concentration = 4 μM in 10 mM $H_2PO_4^-/HPO_4^{2-}$, 0.1 mM EDTA, NaCl, Σ[Na+] = 0.1 M, pH 7.0.

Example D2

Enzymatic hydrolysis of the oligonucleotide according to Example C2. 0.15 O.D.$^{260}$ units of the decanucleotide according to Example C2, or of the natural oligomer dT-10 as standard in 100 μl of the particular buffer A, B or C are incubated in each case with the specified amounts of the particular enzyme, at 37° C. After the specified time the reaction is stopped, the reaction mixture is separated chromatographically by HPLC and the breakdown products are quantified by peak area integration at 260 nm. Table 2 shows the percentage of the total of all cleavage products relative to the total amount of oligonucleotides.

Buffer A (snake venom PDE): 0.1 M tris-HCl, pH 8.5.

Buffer B (nuclease S1): 33 mM sodium acetate, 50 mM NaCl, 0.03 mM $ZnSO_4$, pH 4.5.

Buffer C (calf spleen PDE): 0.1 M ammonium acetate, pH 6.5.

The results are compiled in Table 2 below:

TABLE 2

| Enzyme | Standard decamer (dT-10) | Example C2 | Ratio dT-10:C2 |
|---|---|---|---|
| Snake venom PDE* (EC 3.1.15.1) $1.5 \times 10^{-4}$ U (3'-Exonuclease) | 95% (5 minutes) | 28% (5 minutes) | 3.4 |
| Nuclease S1 (EC 3.1.30.1) 10 U (Exo/Endonuclease) | 100% (5 minutes) | 0 (5 minutes) 20% (60 minutes) | ≧100 |
| Calf spleen PDE (EC 3.1.16.1) a) 0.024 U b) 0.24 U (5'-Exonuclease) | a) 91% (5 minutes) | b) 12% (16 hours) | $2 \times 10^3$ |

*Additionally 5 U alkaline phosphatase (EC 3.1.3.1)

What is claimed is:

1. A compound of the formula I in the form of a racemate or enantiomer thereof,

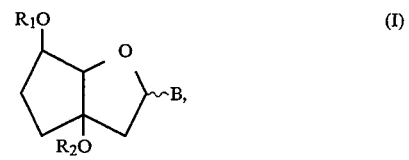 (I)

in which $R_1$ and $R_2$ independently of one another are hydrogen or a protective group, and B is a pyrimidine.

2. A compound of the formula I according to claim 1, in which $R_1$ and $R_2$ are in each case hydrogen.

3. A compound of the formula I according to claim 1, in which $R_1$ and $R_2$ independently of one another are linear or branched $C_1$-$C_8$alkyl, $C_7$-$C_{12}$aralkyl, triphenylsilyl alkyldiphenylsilyl, dialkylphenylsilyl and trialkylsilyl, having 1 to 20 C atoms in the alkyl groups, $C_2$-$C_{12}$acyl, $R_3$-$SO_2$—, in which $R_3$ is $C_1$-$C_{12}$alkyl, $C_5$cycloalkyl or $C_6$cycloalkyl, phenyl, benzyl, $C_1$-$C_{12}$alkylphenyl, $C_1$-$C_{12}$alkylbenzyl, or halophenyl or halobenzyl, or $R_1$ and $R_2$ are $C_1$-$C_{12}$alkoxycarbonyl, phenyloxycarbonyl, benzyloxycarbonyl, methyl- or methoxy- or chlorophenyloxycarbonyl or -benzyloxycarbonyl.

4. A compound of the formula I according to claim 3, in which $R_1$ and $R_2$ independently of one another are linear or branched $C_1$-$C_4$alkyl, $C_7$-$C_{12}$aralkyl, trialkylsilyl having 1 to 12 C atoms in the alkyl groups, $C_2$-$C_8$acyl, $R_3$—$SO_2$—, in which $R_3$ is $C_1$-$C_6$alkyl, phenyl, benzyl, $C_1$-$C_4$alkylphenyl, $C_1$-$C_4$alkylbenzyl, or halophenyl or halobenzyl, or $R_1$ and $R_2$ are $C_1$-$C_8$alkoxycarbonyl, phenoxycarbonyl or benzyloxycarbonyl.

5. A compound of the formula I according to claim 1, in which $R_1$ and $R_2$ are identical protective groups.

6. A compound of the formula I according to claim 1, in which $R_1$ and $R_2$ are methyl, ethyl, n-propyl, i-propyl, n-butyl, i-butyl, t-butyl, benzyl, methylbenzyl, dimethylbenzyl, methoxybenzyl, dimethoxybenzyl, bromobenzyl, diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, tri(methoxyphenyl)methyl, tri(dimethoxyphenyl)methyl, trimethylsilyl, triethylsilyl, tri-n-propylsilyl, i-propyldimethylsilyl, t-butyldimethylsilyl, t-butyldiphenylsilyl, n-octyldimethylsilyl, (1,1,2,2-tetramethylethyl)dimethylsilyl, acetyl, propanoyl, butanoyl, pentanoyl, hexanoyl, benzoyl, methylbenzoyl, methoxybenzoyl, chlorobenzoyl, bromobenzoyl, methylphenylsulfonyl, ethylphenylsulfonyl, propylphenylsulfonyl, butylphenylsulfonyl, phenylphenylsulfonyl, benzylphenylsulfonyl, p-bromophenyl sulfonyl, p-methoxyphenyl)sulfonyl, p-methylphenylsulfonyl, methoxycarbonyl, ethoxycarbonyl, n-propoxycarbonyl, i-propoxycarbonyl, n-butoxycarbonyl, i-butoxycarbonyl, t-butoxycarbonyl, phenyloxycarbonyl, benzyloxycarbonyl, methytphenyloxycarbonyl, methoxyphenyloxycarbonyl, chlorophenyloxycarbonyl, methylbenzyloxycarbonyl, methoxybenzyloxycarbonyl and chlorobenzyloxycarbonyl.

7. A compound of the formula I according to claim 1, in which B in formula I as pyrimidine is a uracil, thymine or cytosine radical of the formulae III, IIIa and IIIb,

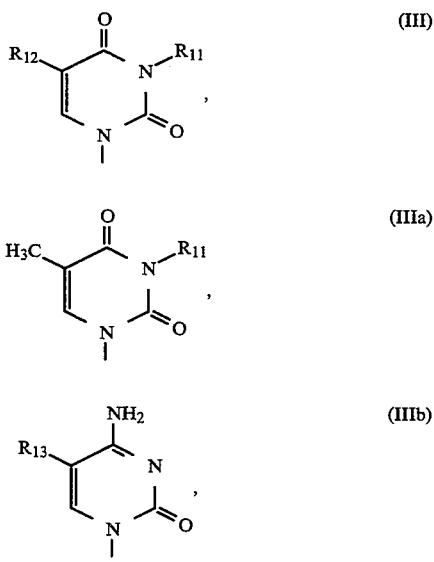

in which $R_{11}$ is H or $C_1$–$C_4$alkyl, and $R_{12}$ and $R_{13}$ independently of one another are H, OH, SH, $NH_2$, $NHNH_2$, NHOH, NHOalkyl having 1 to 12 C atoms, F, Cl, Br, alkyl or hydroxyalkyl or aminoalkyl or alkoxy or alkylthio, having 1 to 12 C atoms, the hydroxyl and amino groups being unsubstituted or substituted by a protective group, or $R_{12}$ and $R_{13}$ are phenyl, benzyl, primary amino having 1 to 20 C atoms or secondary amino having 2 to 30 C atoms, and the hydrogen atoms of the $NH_2$ group in formula IIIb are unsubstituted or substituted by $C_1$–$C_6$alkyl, benzoyl or benzyl, as well as the dihydro derivatives of the radicals of the formulae III, IIIa and IIIb.

8. A compound of the formula I according to claim 7, in which $R_{12}$ is H, $C_1$–$C_6$alkyl or $C_1$–$C_6$hydroxyalkyl, F, Cl, Br, $NH_2$, benzoylamino, mono-di-$C_1$–$C_6$alkylamino.

9. A compound of the formula I according to claim 7 in which $R_{13}$ is H, $C_1$–$C_6$alkyl or $C_1$–$C_6$alkoxy or $C_1$–$C_6$hydroxyalkyl, F, Cl, Br, $NH_2$, benzoylamino, mono- or di-$C_1$–$C_6$alkylamino.

10. A compound of the formula I according to claim 8, in which $R_{12}$ is H, F, Cl, Br, $NH_2$, $NHCH_3$, $N(CH_3)_2$ or $C_1$–$C_4$alkyl.

11. A compound of the formula I according to claim 9, in which $R_{13}$ is H, $C_1$–$C_4$alkyl, $NH_2$, $NHCH_3$ or $(CH_3)_2N$.

12. A compound of the formula I according to claim 1, in which B is uracil, thymine, cytosine, 5-fluorocracil, 5-chlorouracil, 5-bromouracil, dihydrouracil, pseudouracil, 1-methylpseudouracil, 5-methyluracil, 3-methylcytosine or 5-methylcytosine.

13. A compound of the formula I according to claim 1, which is the α- or β-anomer of the formula IV,

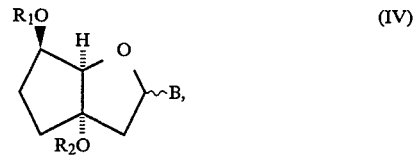

14. A compound of the formula I according to claim, 13, which is the β-anomer of the formula IVa,

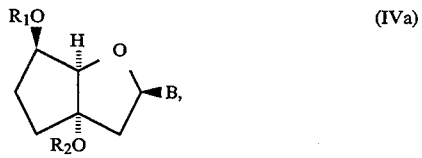

* * * * *